(12) United States Patent
Wang et al.

(10) Patent No.: US 10,703,729 B2
(45) Date of Patent: Jul. 7, 2020

(54) PYRAZINE DERIVATIVE, AND PREPARATION METHOD AND MEDICAL USE THEREOF

(71) Applicant: GUANGZHOU MAGPIE PHARMACEUTICALS CO., LTD., Guangzhou (CN)

(72) Inventors: Yuqiang Wang, Guangzhou (CN); Pei Yu, Guangzhou (CN); Yewei Sun, Guangzhou (CN); Luchen Shan, Guangzhou (CN); Gaoxiao Zhang, Guangzhou (CN); Zaijun Zhang, Guangzhou (CN); Peng Yi, Guangzhou (CN)

(*) Notice: Subject to any disclaimer, the term of this patent is extended or adjusted under 35 U.S.C. 154(b) by 140 days.

(21) Appl. No.: 15/732,796

(22) PCT Filed: Jul. 4, 2016

(86) PCT No.: PCT/CN2016/000360
§ 371 (c)(1),
(2) Date: Dec. 27, 2017

(87) PCT Pub. No.: WO2017/004966
PCT Pub. Date: Jan. 12, 2017

(65) Prior Publication Data
US 2019/0276413 A1    Sep. 12, 2019

(30) Foreign Application Priority Data

Jul. 7, 2015  (CN) .......................... 2015 1 0397137

(51) Int. Cl.
C07D 241/12    (2006.01)
C07D 403/06    (2006.01)
A61K 31/497    (2006.01)

(52) U.S. Cl.
CPC .......... C07D 241/12 (2013.01); A61K 31/497 (2013.01); C07D 403/06 (2013.01)

(58) Field of Classification Search
CPC ... A61K 31/497; C07D 241/12; C07D 403/06
See application file for complete search history.

(56) References Cited

FOREIGN PATENT DOCUMENTS

CN          102311396          *  1/2012

* cited by examiner

*Primary Examiner* — Erich A Leeser
(74) *Attorney, Agent, or Firm* — Panterrain IP Law; Charles Liu

(57) ABSTRACT

The present invention relates to a pyrazine derivative, and preparation method and medical use thereof. The pyrazine derivative can remove free radicals and suppress calcium overload and has cytoprotective effects, and can be used for the prevention and treatment of cardiovascular and cerebrovascular diseases, neurodegenerative diseases and other related diseases.

11 Claims, 8 Drawing Sheets

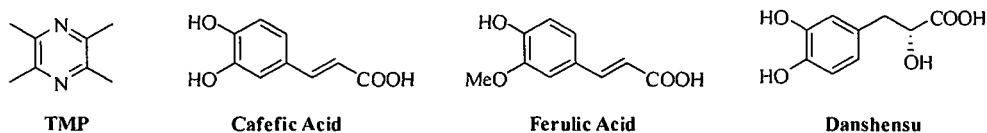

FIG.1

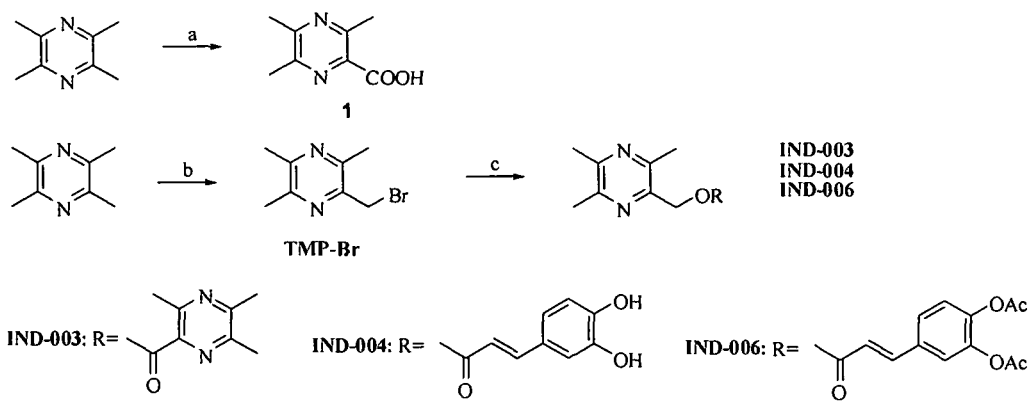

Reagents and conditions: (a) KMnO₄, H₂O, 50 °C, 10 h; (b) NBS, benzoyl peroxide, rt., overnight; (c) K₂CO₃, DMF, rt., 3 h, Compound 1 for IND-003; Cafefic acid for IND-004; (E)-3-(3,4-diacetoxyphenyl)acrylic acid for IND-006.

FIG.2

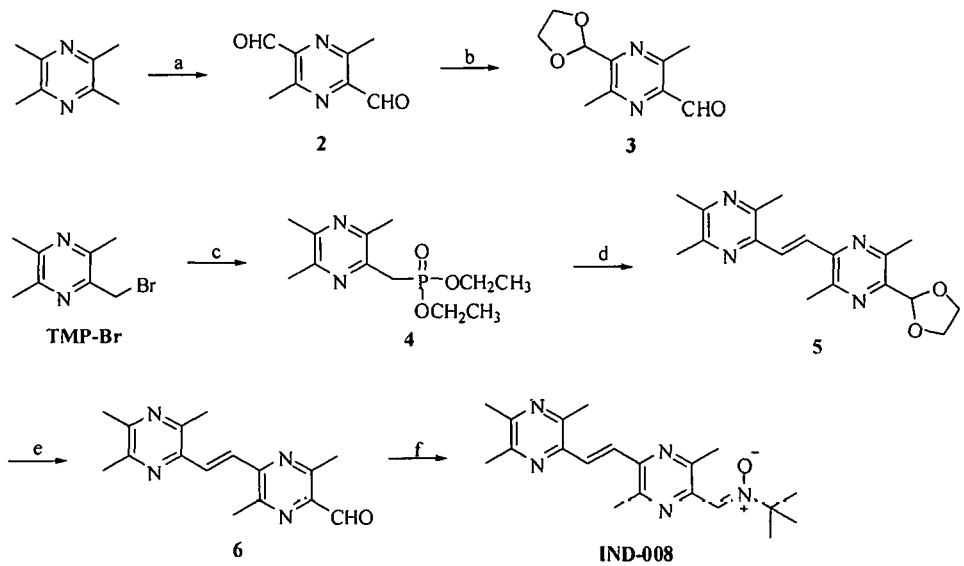

Reagents and conditions: (a) 1,4-diethylene dioxide, SeO₂, 110 °C, 6 h; (b) HOCH₂CH₂OH, MePh, 80 °C, 3 h; (c) (CH₃CH₂O)₃OP, MePh, 110 °C, overnight; (d) NaOCH₃, THF, compound 3, rt., 2 h; (e) Con.HCl/H₂O/THF=2/6/7, rt., 2 h; (f) tert-butylhydroxylamine, CH₃CH₂OH, rt., 4 h.

FIG.3

Reagents and conditions: (a) NaBH(OCOCH₃)₃, DCE, r.t., 4h; (b) PBr₃, DCM, 0 °C, 3 h; (c) HOCH₂CH₂OH, MePh, 80 °C, 3 h; (d) (CH₃CH₂O)₃OP, MePh, 110 °C, overnight; (e) NaOCH₃, THF, compound 3, rt., 2 h; (f) Con.HCl/H₂O/THF=2/6/7, rt., 2 h; (g) tert-butylhydroxylamine, CH₃CH₂OH, rt., 4 h.

Reagents and conditions: (a) Compound 8, K₂CO₃, DMF, rt., 3 h; (b) tert-butylhydroxylamine, CH₃COCH₃, rt., 4 h; (c) DMAP, Ac₂O, rt., overnight.

Reagents and conditions: (a) NaBH4, DCE, rt., overnight; (b) PBr3, DCM, 0 °C, 3 h; (c) 2,5-bis(bromomethyl)-3,6-dimethylpyrazine, NaHCO3, DMF, rt., Cafefic acid, 48 h for IND-021; (E)-3-(3,4-diacetoxyphenyl)acrylic acid, 4 h for IND-022; Sodium danshensu, 2 h for IND-023.

PYRAZINE DERIVATIVE, AND PREPARATION METHOD AND MEDICAL USE THEREOF

FIELD OF THE INVENTION

The present invention relates to a pyrazine derivative or a pharmaceutically acceptable salt thereof, method of preparation thereof and use thereof in medicament manufacture and medical treatments.

BACKGROUND OF THE INVENTION

Tetramethylpyrazine (TMP, also called Chuxiongqin) is a type of alkaloids extracted from herb *Ligusticum wallichii* (Chuanxiong) of traditional Chinese medicine, and has been used for the treatment of coronary heart disease, angina and ischemic cerebrovascular disease (including cerebral thrombosis and cerebral embolism). TMP has certain pharmacological activities. TMP has significant anticoagulant effects. TMP can significantly inhibit the expression of LPS-induced PAI-1 protein and its mRNA in endothelial cells (Song, et al., Chinese Medical J. 113:136, 2000). TMP, in a low-dose, can inhibit the decomposition of phosphatidylinositol and the formation of TXA2, while in a high dose, can inhibit platelet aggregation through combination of glycoprotein IIb/IIIa (Sheu, et al., Thromb Res. 88:259, 1997). TMP has direct thrombolytic effect. Both artery and venous thrombosis models in rats indicate that TMP has anti-thrombolytic effect (Liu and Sylvester, Thromb Res. 58:129, 1990), which may be related to TMP's inhibition on platelet activity, including inhibition of intracellular $Ca^{2+}$ activity, inhibition of phosphate diesterase activity, increase of intracellular cAMP level, and reduction of exposure of glycoprotein IIb/IIIa on the platelet surface (Liu and Sylvester, Thromb Res. 75:51, 1994).

More importantly, TMP has significant effect on protecting nerve cells. TMP may significantly alleviate the MCAo-induced ischemia in rat brain cells, and may significantly remove free radicals produced by human neutrophils. TMP may also protect nerve cells through regulation on the expression of Bcl-2 and Bax to reduce apoptosis (Hsiao, et al. Planta Med. 2006, 72:411-417; Kao, et al. Neurochem Int. 2006, 48:166). TMP is also a calcium channel blocker, and at the same time can facilitate the potassium channel opening. TMP has the effects of inhibiting calcium influx, inhibiting the formation of free radicals, enhancing the activity of superoxide dismutase (SOD), inhibiting lipid peroxidation, and inhibiting inflammatory responses (Zhu, et al., Eur. J. Pharmacol. 510:187, 2005).

Tanshinol (Danshensu) is one of major active ingredients of traditional Chinese medicine salvia miltiorrhiza, and can be used for treating cardiovascular diseases with functions of improving heart function and coronary circulation, anti-coagulation, and improving microcirculation, and also has effects of such as anti-inflammation, anti-tumor, resisting cerebral thrombosis, and protecting liver. With an o-diphenol hydroxyl and o-hydroxy-carboxylic acid structure, Danshensu is extremely easy to be oxidized and deteriorated, and thus is hard to be stored. The polar groups of Danshensu may be bonded to such as glucuronic acid and be excreted with the urine. The in vitro half-life of Danshensu is very short, bioavailability is only 9.53-14.18%, such that repetitive administrations may be necessary and the clinical application is limited (Wang Tingfang, Journal of Pharmaceutical Practice, 29 (2): 83-87, 2011).

Caffeic acid, as a polyhydroxy styrene acid compound, is widely found in some botanical food such as tomatoes, carrots, strawberry, blueberry and cereals, and Chinese herbal medicines. Caffeic acid has various pharmacological effects of such as anti-inflammation, antibacterial, and improving white blood cell and bold plate, and thus can be used for preventing and treating various diseases associated with oxidative stress, inflammatory reaction and viral infection, such as cardiovascular diseases, brain tissue damage, human immunodeficiency virus (HIV) infection, and leucopenia and thrombocytopenia (Prasad N R, et al. J Photochem Photobiol B, 2009, 95 (3): 196-203). Although having good pharmacological effects, caffeic acid is also very prone to oxidative deterioration, and is difficult to store. Caffeic acid has a structure containing phenolic hydroxyl groups and carboxyl groups and thus can be excreted with urine in the form of glucuronic acid and sulfuric acid conjugates and the like (Gumbinger H G, et al. Planta Med, 1993, 59 (6): 491-493), such that the in vivo half-life is also very short and repetitive drug administration would be required, which limits its clinical applications.

Oxidative stress refers to the body when subjected to a variety of harmful stimuli, the oxidation system and anti-oxidation system becomes imbalance, the degree of oxidation exceeds the oxide scavenging capacity, resulting in tissue damage. Oxidative stress plays a very important role in the pathogenesis of many diseases and aging. The accumulation of reactive oxygen species can cause nucleic acid cleavage, enzymatic inactivation, polysaccharide depolymerization, lipid peroxidation, eventually leading to tissue damage and even death (Yan et al. Free Radic Biol Med. 2013, 62:90-101). Because oxidative stress causes the body to be in a vulnerable state, it also enhances the virulence of the causative agent and can lead to gene mutations (Beck M A. Proe Nutr Soe. 1999, 58 (3): 707-711). It is currently believed that oxidative stress is closely related to various neurodegenerative diseases including Parkinson's disease (PD) and Alzheimer's disease (AD).

The most common cardiovascular and cerebrovascular diseases generally include coronary heart disease and stroke. Suc diseases are due to arterial stenosis, and caused by insufficient blood supply. The arterial intimal damage, lipid deposition, and platelet and fibrin deposition on lipid plaque may result in thickening of the vessel wall, narrowing of the vascular lumen, and leading to arterial wall atherosclerosis. Sclerosis plaque thrombosis may cause blockage of blood vessels, triggering ischemic heart disease or ischemic cerebrovascular diseases. If blood flow is not restored within 20-40 minutes, it can cause irreversible death of cardiomyocytes or brain cells. During ischemia, a portion of electrons detach from the oxidized respiratory chain of mitochondria and transfer oxygen molecules to form superoxide anions ($O_2.^-$). The superoxide anions are very active and can be further subjected to enzymatic catalytic or metal catalytic reactions with other molecules to form secondary ROS, including free radicals of .OH, ROO., $H_2O_2$ and $ONOO^-$ (Miller et al. Free Radic. Biol. 8:95-108.; Valko et al. Curr. Med. Chem. 2005, 12:1161-1208). These free radicals can destabilize biofilms such as mitochondrial membranes and cell membranes, causing protein denaturation, DNA damage and apoptosis (Siems et al. Life Sci. 1995, 57: 785-789; Stadtman. Curr. Med. Chem. 2004, 11:1105-1112).

Neurodegenerative diseases are related to a progressive condition of irreversible loss of neurons in brain or spinal cord. The irreversible loss of neurons or their myelin sheaths may cause functional disorder. Common neurodegenerative diseases include cerebral ischemia, Parkinson's disease, Alzheimer's disease, amyotrophic lateral sclerosis and the like. The pathogenesis of neurodegenerative diseases is extremely complex. The neuronal damage is related to many factors such as oxidative stress, calcium overload, inflammatory reaction and apoptosis.

SUMMARY OF THE INVENTION

The present invention is directed to a pyrazine derivative and a pharmaceutically acceptable salt thereof, having strong nerve protective effects.

The invention is also directed to a method of preparation of the pyrazine derivative.

The invention is further directed to a use of the pyrazine derivative and a pharmaceutical composition thereof for the manufacture of medicaments and the treatment of diseases.

In one aspect, the present invention provided a pyrazine derivative of formula I:

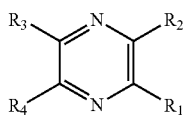

or pharmaceutically acceptable salts thereof, wherein:

$R_1$, $R_2$, $R_3$ and $R_4$, being the same or different, are each independently hydrogen, saturated or unsaturated alkyl, cycloalkyl, substituted or unsubstituted aryl, heteroaryl, nitronyl or a group selected from R'COO, R'COOCH(R"), R'CH=CH, R'CONH, R'CONH(R"), wherein R' and R" are each independently saturated or unsaturated alkyl, cycloalkyl, substituted or unsubstituted aryl or heteroaryl;

with a proviso that all $R_1$, $R_2$, $R_3$ and $R_4$ cannot simultaneously be hydrogen, methyl or nitronyl;

$R_1$ and $R_3$ cannot both be nitronyl, and $R_2$ and $R_4$ cannot both be nitronyl.

In some embodiments of the pyrazine derivative as described in formula I, both $R_2$ and $R_4$ are methyl, such that the pyrazine derivative can be further defined as of formula II:

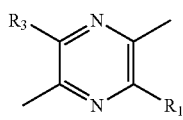

wherein:

$R_1$ and $R_3$, being the same or different, are each independently hydrogen, saturated or unsaturated alkyl, cycloalkyl, substituted or unsubstituted aryl, heteroaryl, nitronyl or a group selected from R'COO, R'COOCH(R"), R'CH=CH, R'CONH, R'CONH(R"), wherein R' and R" are each a saturated or unsaturated alkyl, cycloalkyl, substituted or unsubstituted aryl or heteroaryl;

with a proviso that $R_1$ and $R_3$ cannot both be hydrogen, methyl or nitronyl.

In some embodiments of the pyrazine derivative as described in formula II, $R_3$ is methyl or nitronyl group, such that the pyrazine derivative can be further defined as of formula III or IV:

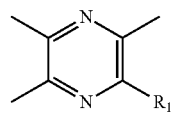

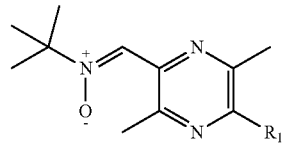

wherein:

$R_1$ is selected from saturated or unsaturated alkyl, cycloalkyl, substituted or unsubstituted aryl, heteroaryl, or a group selected from R'COO, R'COOCH(R"), R'CH=CH, R'CONH, R'CONH(R"), wherein R' and R" are each a saturated or unsaturated alkyl, cycloalkyl, substituted or unsubstituted aryl or heteroaryl;

with a proviso that $R_1$ cannot be hydrogen, methyl or nitronyl.

Further, in some embodiments, the pyrazine derivative represented by formula I may further have a formula V:

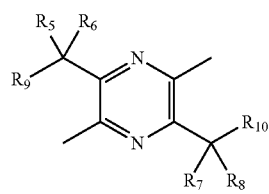

wherein:

$R_5$, $R_6$, $R_7$, $R_8$, being the same or different, are each independently hydrogen, saturated or unsaturated alkyl, cycloalkyl, substituted or unsubstituted aryl, or heteroaryl;

$R_9$ and $R_{10}$, being the same or different, are each independently selected from the group consisting of hydrogen, R'''COO, R'''CONH, wherein R''' is a saturated or unsaturated alkyl, cycloalkyl, substituted or unsubstituted aryl, or heteroaryl group;

with a proviso that $R_5$, $R_6$, $R_7$, $R_8$, $R_9$ and $R_{10}$ cannot all be hydrogen.

In some preferred embodiments, the pyrazine derivative of formula V may further have a formula VI, VII or VIII:

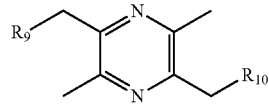

-continued

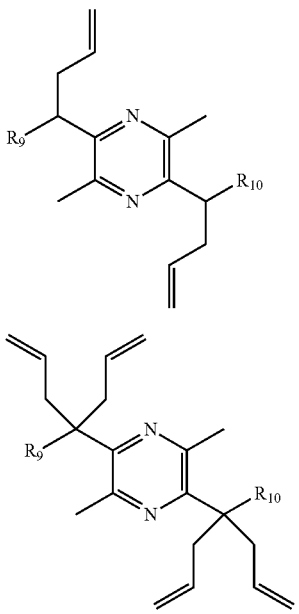

wherein:

$R_9$ and $R_{10}$, being the same or different, are each independently selected from the group consisting of hydrogen, R'''COO, R''' CONH, wherein R''' is saturated or unsaturated alkyl, substituted or unsubstituted aryl, or heteroaryl;

with a proviso that $R_9$ and $R_{10}$ cannot both be hydrogen.

In addition, the pyrazine derivative and a pharmaceutically acceptable salt thereof as described herein can form a pharmaceutical composition, comprising a therapeutically effective amount of the pyrazine derivative of any one of claims 1 to 7 as an active pharmaceutical ingredient, and a pharmaceutically acceptable carrier and excipient.

In another aspect, the present invention provided a method of preparation of the pyrazine derivative as described herein, the method comprising:

tetramethylpyrazine is first reacted with NBS to give a ligustrazine mono-bromide as intermediate I; or tetramethylpyrazine is oxidized by activated manganese dioxide to give a para-substituted tetramethylpyrazine dialdehyde derivative, which is subjected to selective reduction, bromination and aldehyde group protection to give a para-substituted tetramethylpyrazine derivative as intermediate II; and the intermediate I or intermediate II is further reacted to give a respective product of the pyrazine derivative.

In some embodiments, the method may further comprise:

the intermediate I or intermediate II is reacted with triethyl phosphate to give intermediate III or intermediate IV, respectively;

the tetramethylpyrazine dialdehyde derivative is reacted with ethylene glycol, with one of aldehyde groups being selectively protected, to give a product, which is further reacted respectively with the intermediate III or the intermediate IV to give a respective tetramethylpyrazine coupling compound, which is deprotected under acidic conditions and then reacted with t-butylhydroxylamine to give a product of the pyrazine derivative.

In some embodiments, the method may further comprise:

the tetramethylpyrazine dialdehyde derivative is reacted with one or two of aldehyde groups being selectively reduced to give a monohydroxy derivative or a dihydroxy derivative;

the monohydroxy derivative or the dihydroxy derivative is each reacted with phosphorus tribromide to give a monobromo or dibromo derivative, respectively;

the mono-bromo derivative is condensed with a different carboxylic acid and then reacted with t-butylhydroxylamine, or the dibromo derivative is reacted with a different carboxylic acid or sodium carboxylate to give a product of the pyrazine derivative.

Further, the pyrazine derivative as described herein has strong free radical scavenging and cytoprotective effects, and can be used in manufacture of medicaments for the prevention and treatment of diseases caused by nerve damage and excessive radicals. The medicament may comprise a therapeutically effective amount of the compound of formula I or a pharmaceutically acceptable salt thereof.

Unless defined otherwise, all technical and scientific terms and phrases used herein have the meaning commonly understood by one of ordinary skill in the pertinent art, while the following terms and phrases as used herein are intended to have the following meanings.

As used herein, the term "alkyl" refers to unsubstituted or substituted straight, branched or cyclic alkyl having up to 10 carbon atoms. The straight alkyl includes, for example, methyl, ethyl, n-propyl, n-butyl, n-pentyl, n-hexyl, n-heptyl, and n-octyl. The cyclic alkyl ("cycloalkyl") includes, for example, cyclopropyl, cyclobutyl, cyclopentyl, and cyclohexyl. Alkyl can be substituted with one or more substituents. The non-limiting examples of the substituents include $NH_2$, $NO_2$, $N(CH_3)_2$, $ONO_2$, F, Cl, Br, I, OH, $OCH_3$, $CO_2H$, $CO_2CH_3$, CN, aryl, and hetroaryl. The term "alkyl" also refers to unsubstituted or substituted straight, branched or cyclic alkyl having up to 10 carbon atoms and at least one heteroatom (e.g., nitrogen, oxygen, or sulfur). The straight-chain alkyls include, for example, $CH_2CH_2OCH_3$, $CH_2CH_2N(CH_3)_2$, and $CH_2CH_2SCH_3$. The branched alkyls include, for example, $CH_2CH(OCH_3)CH_3$, $CH_2CH(N(CH_3)_2)CH_3$, and $CH_2CH(OCH_3)CH_3$. The cyclic alkyls include, for example, $CH(CH_2CH_2)_2O$, $H(CH_2CH_2)_2NCH_3$, and $CH(CH_2CH_2)_2S$. The alkyl can be also substituted with one or more substituents, the non-limiting examples of which include $NH_2$, $NO_2$, $N(CH_3)_2$, $ONO_2$, F, Cl, Br, I, OH, $OCH_3$, $CO_2H$, $CO_2CH_3$, CN, aryl, and heteroaryl.

The term "aryl" as used herein refers to unsubstituted or substituted aromatic compounds and carbocyclic groups. The aryl can be either a monocyclic compound or a fused polycyclic compound. For example, phenyl is a monocyclic aryl, and naphtyl is a fused polycyclic aryl. The aryl can be substituted with one or more substituents, the non-limiting examples of which include $NH_2$, $NO_2$, $N(CH_3)_2$, $ONO_2$, F, Cl, Br, I, OH, $OCH_3$, $CO_2H$, $CO_2CH_3$, CN, aryl, and heteroaryl.

The heteroaryl relates to substituted or an unsubstituted monocyclic or polycyclic group, where the ring contains at least one heteroatom, such as nitrogen, oxygen and sulfur. For example, a typical heteroaryl includes one or more nitrogen atoms such as in tetrazolyl, pyrrolyl, pyridyl (e.g., pyrid-4-yl, pyrid-3-yl, pyrid-2-yl), pyridazinyl, indyl, quinolyl (e.g., quinol-2-yl, quinol-3-yl), imidazolyl, isoquinolyl, pyrazolyl, pyrazinyl, pyrimidinyl, pyridonyl and pyridazinyl; a typical hetroaryl includes at least one oxygen atom such as in fur-2-yl, fur-3-yl and benzofuryl; a typical hetroaryl includes at least one surfur atom such as in thienyl and benzothienyl; a typical heteroaryl containing more than one kind of heteroatoms includes furoazetidinyl, oxazolyl, isoxazolyl, thiazolyl and phenothioxinyl. The heteroaryl can be substituted by one or more substituents which include but not limited to $NH_2$, $NO_2$, O-alkyl, NH-alkyl, $N(alkyl)_2$, NHC(O)-alkyl, $ONO_2$, F, Cl, Br, I, OH, $OCF_3$, $OSO_2CH_3$, $CO_2H$, $CO_2$-alkyl, CN, aryl, and polyaryl. Furthermore, the heteroaryl also includes those with a heteroatom in the ring being oxidized, for example, to form N-oxide, ketone, or sulfone.

The term "nitrones" refer to nitroxides of imines containing different substituents on N, and these substituents include different alkyl, cycloalkyl, aryl and heteroaryl groups.

The phrase "pharmaceutically acceptable" means that a compound, such as a salt or excipient, has no unacceptable toxicity. Examples of pharmaceutically acceptable salts include, but are not limited to, inorganic anions, such as chlorine ion, bromine ion, iodine ion, sulfuric acid radical, sulfurous acid radical, nitric acid radical, nitrous acid radical and phosphoric acid radical; and organic anions, such as acetic acid radical, pyruvic acid radical, propionic acid radical, cinnamic acid radical, tosylic acid radical, citric acid radical, lactic acid radical and gluconic acid radical. Pharmaceutically acceptable excipients are described below, and also in the reference of: E. W. Martin, in Remington's Pharmaceutical Sciences Mack Publishing Company (1995), Philadelphia, Pa., $19^{th}$ ed.

The present invention is related to new compounds comprise those of formula I. The pyrazine derivative of formula I can be used for removing free radicals including superoxide anions ($O_2.^-$), oxygen-containing nitrates ($ONOO^-$) and hydroxyl radicals (.OH). On the other hand, the pyrazine derivative can be used to protect nerve cells. So that the pyrazine derivative can be used for prevention and treatment of cardiovascular and cerebrovascular diseases, which include cerebral apoplexy, trauma, hypoxic-ischemic brain injury, cerebral hemorrhage, ischemic heart disease, angina pectoris, blood vessel embolism, atherosclerosis, apoplexy sequelae, acute myocardial infarction, cardiopulmonary lateral flow, respiration distress syndrome, cardiac ischemia or reperfusion, toxic shock syndrome, adult respiratory distress syndrome, cachexia, myocarditis, coronary heart disease or heart disease; the glutamate receptor related diseases, which include Alzheimer's disease, Parkinson's disease, Huntington's disease, amyotrophic lateral sclerosis, myasthenia gravis, glaucoma, dementia, hyperthyroidism, hypertension, bronchial asthma, type IV hyperlipoproteinemia or kidney functional failure; the oxidative stress injury/free radical related diseases, which include stroke, traumatic brain injury, epilepsy, Parkinson's disease, Huntington's disease, amyotrophic lateral sclerosis, Alzheimer's disease, hypoxic-ischemic brain damage, cerebral hemorrhage, dementia, ischemic heart disease, blood vessel embolism, atherosclerosis, hypercholesterolemia, emphysema, cataract, diabetes, acute pancreatitis, alcohol-induced liver disease, kidney damage or cancer; the neurodegenerative diseases, which include cerebral ischemia, Parkinson's disease, Alzheimer's disease, amyotrophic lateral sclerosis, ataxia telangiectasia, bovine spongiform encephalopathy, Creutzfeldt-Jakob Disease, Huntington's disease, cerebellar atrophy, multiple sclerosis, primary lateral sclerosis or spinal muscular atrophy; the inflammatory infectious diseases, include inflammatory bowel disease, diabetes, rheumatoid arthritis, asthma, cirrhosis, allograft, encephalomyelitis, meningitis, peritonitis, vasculitis, lymphocytic choriomeningitis, choriomeningitis, glomerulonephritis, systemic lupus erythematosus, gastrointestinal motility disorder, obesity, hunger disease, hepatitis, renal failure, cardiopulmonary bypass, respiratory distress syndrome, cardiac ischemia or reperfusion, toxic shock syndrome, adult respiratory distress syndrome, cachexia, myocarditis, atherosclerosis, coronary heart disease, sudden cardiac heart, diabetic retinopathy, uveitis, glaucoma, blepharitis, chalazion, allergic eye disease, corneal ulcer, keratitis, cataracts or age-related macular degeneration or optic neuritis ophthalmic diseases.

The pyrazine derivatives as described herein may be administered to a patient as a pharmaceutically acceptable salt or a pharmaceutical composition. The phrase "therapeutically effective amount" is intended to include an amount of a drug such as a Danshensu derivative described herein in which the drug shows biological activity as used to treat or prevent a disease.

The compounds as described herein can be prepared in different dosage forms, which include solid, semi-solid, liquid, and aerosol (Remington's Pharmaceutical Sciences, Mack Publishing Company (1995), Philadelphia, Pa., $19^{th}$ ed). These dosage forms can be further divided into more specific forms, including tablet, pill, sugar lozenge, granule, gel, paste, solution, suppository, injection, inhalant and spray. These dosage forms can be used for local or systemic administration and for immediate-release or sustained release. There are many routes of administration of these drugs, which include oral, buccal, rectal, peritoneal, intraperitoneal, transdermal administration, subcutaneous and endotracheal administrations.

For administration via injection, the compound or composition as described herein may be prepared, by using a water-soluble or lipid-soluble solvent, into a solution, suspension or emulsion. The lipid-soluble solvent can be, for example, plant oil, synthetic fatty acid glyceride, higher fatty acid ester and/or proylene glycol. The compounds as described herein are more readily dissolved in Hank's solution, Ringer's solution or physiological saline.

When applied through oral administration, the compound or composition as described herein can be prepared through certain common techniques into a complex by adding a pharmaceutical acceptable excipient. Such excipients can be used to prepare these compounds into different dosage forms, such as tablet, pill, suspension, and gel. There are many ways for oral preparation, for example, by mixing the compound and the solid excipient, grinding fully the resulting mixture, adding appropriate auxiliary agents, and processing the mixture into particles. The auxiliary agents, which can be used for oral preparation, include, for example, sugars such as lactose, sucrose, mannitol, or sorbitol; celluloses such as corn starch, wheat starch, potato starch, gelatin, gummi tragacanthae, methyl cellulose, hydroxyproylmethyl-cellulose, sodium carboxymethyl cellulose, and polyethylene pyrrole ketones.

The compounds as described herein can be prepared also in the form of spray, which can be achieved by using a pressurizer and a sprayer or dry powder inhaling device. Suitable spray agents used for spraying include, for example, dichlorodifluoromethane, fluorine chloroform, dichloro-tetrafluoroethane, carbon dioxide, and dimethyl ether. The amount of spray delivered from a sprayer can be controlled by the adjustment of the injecting valve of the sprayer.

The dosage forms as described herein are all related to the therapeutically effective amount of the compounds of the invention. The therapeutically effective amount of the compounds as described herein may depend on specific conditions of patients under the treatment. To determine the appropriate dose, various factors much be taken into account, for example, the route of administration to be used, weight and conditions of the patient to be treated, and observation and subjective judgment made by the prescribing physician. The therapeutically effective amount is usually determined by an experienced prescribing physician.

The present invention provided pyrazine derivative with a novel structure and a pharmaceutically acceptable salt thereof through chemical modification of pyrazine. The pyrazine derivative as provided herein has multiple functions (elimination of free radicals and cytoprotection) and enhanced stability. The core structure of the molecule is kept to maintain the integrity of the active site and, at the same time, to enhance the medical effect. These compounds are promising new drugs for the prevention and treatment of neurological, infectious, metabolic, cardiovascular, and degenerative diseases.

The novel pyrazine derivative and pharmaceutically acceptable salt thereof as described herein showed some advantages for medical purposes:

Tetramethylpyrazine (Chuanxongqin), based on drug combination principle, is used to construct in combination with other active ingredients of traditional Chinese medicine, and the resulting compound showed much higher the biological activity than that of the active ingredients of traditional Chinese medicine.

By introducing a nitronyl group, as indicated herein, the pyrazine derivative showed improved ability for removing free radicals, in a way much more effectively than that of the traditional Chinese medicine.

By introducing a substituent beside the ester bond, as indicated herein, the pyrazine derivative showed higher stability to overcome the in vivo instability problem of some compounds of esters.

BRIEF DESCRIPTION OF THE DRAWINGS

FIG. 1 shows the structures of the compounds TMP, caffeic acid, ferulic acid and Danshensu, respectively;

FIG. 2 illustrates the synthesis of the compounds IND-003, IND-004 and IND-006;

FIG. 3 illustrates the synthesis of the compound IND-008;

DETAILED DESCRIPTION OF THE EMBODIMENTS

Figure 4:
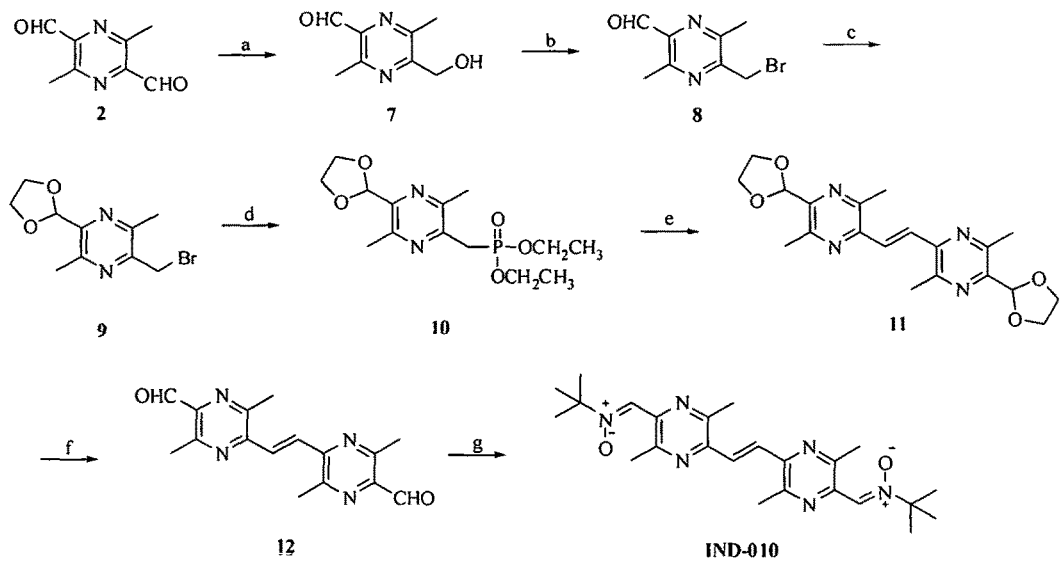
FIG. 4 illustrates the synthesis of the compound IND-010.

The present invention will be further described in detail below with reference to the accompanying drawings and embodiments. The following examples are intended for illustration only and are not intended to limit the scope of the invention in any way.

Example 1. Synthesis of Compound IND-003 (FIG. 2)

TMP (13.6 g, 100.0 mmol) was dissolved in 300 mL of water, $KMnO_4$ (31.6 g, 200.0 mmol) was added in portions, and the reaction was heated to 50° C. for 10 hours. After the reaction was completed, the resulting material was cooled and extracted with ethyl acetate. The organic phase was discarded, and the aqueous phase was adjusted to pH 3 with 10% hydrochloric acid and extracted with ethyl acetate, dried over anhydrous sodium sulfate and evaporated to dryness under reduced pressure to give 3,5,6-trimethylpyrazine-2-carboxylic acid as a yellow solid (Compound 1) (9.6 g, 57.8%). ESI-MS: $[M+H]^+$ m/z 167.0.

TMP (15 g, 110.3 mmol) was dissolved in 250 mL of carbon tetrachloride, then NBS (20 g, 112.4 mmol) and a catalytic amount of benzoyl peroxide were added respectively. The reaction was heated to 80° C. overnight. After the reaction was completed, an appropriate amount of water was added, and the resulting mixture was extracted with ethyl acetate, dried over anhydrous sodium sulfate. The solvent was evaporated to dryness under reduced pressure. The resulting material was separated via column chromatography (ethyl acetate:petroleum ether=1:9) to give TMP-Br as a pale white solid (12.6 g, 53.2%). ESI-MS: $[M+H]^+$ m/z 217.0. $^1$H-NMR: (300 MHz, $CDCl_3$) δ: 4.67 (s, 2H), 2.53 (s, 6H), 2.41 (s, 3H).

Compound 1 (0.4 g, 2.4 mmol) was dissolved in 10 ml of N,N-dimethylformamide, and TMP-Br (0.43 g, 2.0 mmol) and potassium carbonate (0.42 g, 3.0 mmol) were added respectively. The reaction was run for 3 hours at room temperature. After the reaction was completed, an appropriate amount of water was added. The resulting mixture was extracted with ethyl acetate, dried over anhydrous sodium sulfate, and the solvent was evaporated to dryness under reduced pressure. The resulting material was separated via column chromatography (ethyl acetate:petroleum ether=1:2) to give IND-003 as a pale white solid (0.41 g, 68.7%). ESI-MS: $[M+H]^+$ m/z 301.3. $^1$H-NMR:(300 MHz, $CDCl_3$) δ: 5.51 (s, 2H), 2.75 (s, 3H), 2.61 (s, 3H), 2.57 (d, J=1.9 Hz, 6H), 2.52 (s, 3H), 2.50 (s, 3H). $^{13}$C-NMR: 165.66, 154.68, 151.36, 151.23, 149.38, 149.06, 148.76, 144.37, 65.81, 22.56, 22.24, 21.71, 21.57, 21.45, 20.63. Anal. ($C_{16}H_{20}N_4O_2$) C, H, C; found C 64.16%, H 7.019%, N 18.56%; requires: C 63.98%, H 6.71%, N 18.65%.

Example 2. Synthesis of Compound IND-004 (FIG. 2)

Caffeic acid (0.36 g, 2 mmol) was dissolved in 10 ml of N,N-dimethylformamide, and $K_2CO_3$ (0.31 g, 2.4 mmol) and TMP-Br (0.43 g, 2 mmol) were added respectively. The reaction was stirred at room temperature for 2 hours. After the reaction was completed, an appropriate amount of water was added. The resulting mixture was extracted with ethyl acetate, dried over anhydrous sodium sulfate, and solvent was evaporated to dryness under reduced pressure. The resulting material was separated with column chromatography (ethyl acetate:petroleum ether=1:1) to give compound IND-004 as a white solid (0.36 g, 57%). ESI-MS: [M+H]$^+$ m/z 315.23. $^1$H-NMR:(300 MHz, DMSO-d6) δ: 9.62 (s, 1H), 9.16 (s, 1H), 7.50 (d, J=15.9 Hz, 1H), 7.05 (d, J=1.8 Hz, 1H), 7.01 (dd, J=8.1, 1.8 Hz, 1H), 6.76 (d, J=8.1 Hz, 1H), 6.32 (d, J=15.9 Hz, 1H), 5.24 (s, 2H), 2.48 (s, 3H), 2.44 (s, 3H), 2.42 (s, 3H). $^{13}$C-NMR: 166.72, 151.27, 149.06, 149.00, 148.90, 146.20, 146.03, 145.34, 125.90, 122.00, 116.18, 115.39, 113.83, 64.86, 21.69, 21.47, 20.58. Anal. ($C_{17}H_{18}N_2O_4$) C, H, C; found C 64.92%, H 5.714%, N 8.83%; requires: C 64.96%, H 5.77%, N 8.91%.

Example 3. Synthesis of Compound IND-006 (FIG. 2)

(E)-3-(3,4-acetoxyl phenyl) acrylic acid (0.53 g, 2 mmol) was dissolved in 10 ml of N,N-dimethylformamide, and $K_2CO_3$ (0.31 g, 2.4 mmol) and TMP-Br (0.43 g, 2 mmol) were added respectively. The reaction was stirred at room temperature for 2 hours. After the completion of reaction, an appropriate amount of water was added. The resulting mixture was extracted with ethyl acetate, dried over anhydrous sodium sulfate, and the solvent was evaporated to dryness under reduced pressure. The resulting material was separated with column chromatography (ethyl acetate:petroleum ether=1:1) to give compound IND-006 as a white solid (0.60 g, 75%). ESI-MS: [M+H]$^+$ m/z 399.28. $^1$H-NMR:(300 MHz, CDCl$_3$) δ: 7.65 (d, J=15.9 Hz, 1H), 7.40 (dd, J=8.4, 2.1 Hz, 1H), 7.35 (d, J=2.1 Hz, 1H), 7.21 (d, J=8.4 Hz, 1H), 6.43 (d, J=15.9 Hz, 1H), 5.53 (s, 2H), 2.57 (s, 3H), 2.52 (s, 6H), 2.30 (s, 6H). $^{13}$C-NMR: 168.06, 167.98, 166.17, 151.43, 149.14, 144.72, 143.60, 143.57, 142.43, 133.12, 126.44, 123.96, 122.82, 118.58, 65.29, 21.70, 21.46, 20.66, 20.61, 20.56. Anal. ($C_{21}H_{22}N_2O_6$) C, H, C; found C 63.46%, H 5.630%, N 6.88%; requires: C 63.31%, H 5.57%, N 7.03%.

Example 4. Synthesis of Compound IND-008 (FIG. 3)

TMP (25 g, 183.8 mmol) was dissolved in 250 mL of 1,4-dioxane, and selenium dioxide (40.8 g, 367.6 mmol) was added, and the reaction was heated to 110° C. for 6 hours. After the reaction was completed, the reaction solution was filtered, and an appropriate amount of silica gel was added to the filtrate. The solvent was evaporated to dryness under reduced pressure. The residue was separated by column chromatography (ethyl acetate:petroleum ether=1:15) to give 3,6-dimethyl pyrazine-2,5-dicarbaldehyde (Compound 2) as a brownish solid (11.4 g, 37.9%). ESI-MS: [M+H]$^+$ m/z 165.0. $^1$H-NMR:(300 MHz, CDCl$_3$) δ: 10.22 (s, 2H), 2.92 (s, 6H).

Compound 2 (5 g, 30.5 mmol) was dissolved in 50 ml of toluene, and then ethylene glycol (1.89 g, 30.5 mmol) and a catalytic amount of p-toluene sulfonic acid were added respectively. The reaction was heated to 80° C. for 3 hours. After the reaction was completed, methylbenzene was evaporated, and an appropriate amount of water was added. The resulting mixture was extracted with ethyl acetate, dried over anhydrous sodium sulfate, and the solvent was evaporated to dryness under reduced pressure. The resulting material was separated with column chromatography (ethyl acetate:petroleum ether=1:5) to give Compound 3 as a yellow solid (3.15 g, 49.6%). ESI-MS: [M+H]$^+$ m/z 209.0. $^1$H-NMR:(300 MHz, DMSO) δ: 10.08 (s, 1H), 5.96 (s, 1H), 4.13 (m, 4H), 2.72 (s, 3H), 2.63 (s, 3H).

Compound TMP-Br (1.86 g, 8.8 mmol) was dissolved in 30 mL of toluene, and triethyl phosphite (2.8 g, 17.6 mmol) was added. The reaction was heated to 110° C. overnight. After completion of the reaction, methylbenzene was evaporated, and an appropriate amount of water was added. The resulting mixture was extracted with ethyl acetate, dried over anhydrous sodium sulfate, and the solvent was evaporated under reduced pressure to give compound 4 as a colorless oily (1.72 g, 72.9%). ESI-MS: [M+H]$^+$ m/z 273.1.

Compound 4 (1.2 g, 4.4 mmol) was dissolved in 20 mL of dichloromethane, and Compound 3 (0.92 g, 4.4 mmol) and sodium methoxide (0.72 g, 13.4 mmol) were added respectively. The reaction was run for 2 hours at room temperature. After the reaction was completed, an appropriate amount of water was added. The resulting mixture was extracted with ethyl acetate, dried over anhydrous sodium sulfate. The organic solvent was evaporated, and the resulting material was used directly in the next reaction directly without further purification. ESI-MS: [M+H]$^+$ m/z 327.10.

The above resulting material was dissolved in 20 mL of a liquid mixture (Con.HCl:H$_2$O:THF=2:6:7), and the reaction was run at room temperature for 2 hours. After the reaction was completed, the organic solvent is partially evaporated under reduced pressure, and an appropriate amount of water was added. The resulting mixture was extracted with ethyl acetate, dried over anhydrous sodium sulfate, and the solvent was evaporated to dryness under reduced pressure. The resulting material was separated with column chromatography (ethyl acetate:petroleum ether=1:10) to give Compound 6 as a yellow solid (0.67 g). ESI-MS: [M+H]$^+$ m/z 283.20.

Compound 6 (0.5 g, 1.8 mmol) was dissolved in 10 mL of ethanol, and tert-butyl hydroxylamine (0.32 g, 3.55 mmol) was added. The reaction was run at room temperature for 4 hours. After the reaction was completed, the organic solvent was evaporated under reduced pressure, and an appropriate amount of water was added. The resulting mixture was extracted with ethyl acetate, dried over anhydrous sodium sulfate, and the solvent was evaporated to dryness under reduced pressure. The resulting material was separated with column chromatography (ethyl acetate:petroleum ether=1:10) to give IND-008 as a yellow solid (0.21 g, 33%). ESI-MS: [M+H]$^+$ m/z 354.30. $^1$H-NMR:(300 MHz, CDCl$_3$) δ: 8.05 (d, J=15.0 Hz, 1H), 7.98 (d, J=15.0 Hz, 1H), 7.86 (s, 1H), 2.71 (d, J=6.6 Hz, 6H), 2.57 (s, 6H), 2.54 (s, 3H), 1.66 (s, 9H). $^{13}$C-NMR: 150.86, 150.70, 149.41, 148.34, 147.76, 147.94, 144.94, 144.63, 142.37, 130.13, 128.20, 127.3, 28.23, 25.29, 21.92, 21.85, 21.06, 20.99. Anal. ($C_{20}H_{27}N_5O$) C, H, C; found C 67.83%, H 7.628%, N 19.32%; requires: C 67.96%, H 7.70%, N 19.81%.

Example 5. Synthesis of Compound IND-010 (FIG. 4)

Compound 2 (5 g, 30.5 mmol) was dissolved in 80 ml of 1,2-dichloroethane, and triacetoxy sodium borohydride (5.2 g, 24.4 mmol) was added in batches. The reaction was run at room temperature for about 4 hours. After the reaction was completed, the resulting material was filtered, and to the filtrate was added with an appropriate amount of silica gel, and the solvent was evaporated to dryness under reduced pressure. The resulting material was separated by column chromatography (ethyl acetate:petroleum ether=1:3) to give as a white solid (2.1 g, 41.2%). ESI-MS: [M+H]$^+$ m/z 167.1. $^1$H-NMR:(300 MHz, DMSO-d6) δ: 10.08 (s, 1H), 5.43 (m, 1H), 4.67 (d, J=5.7 Hz, 1H), 2.73 (s, 3H), 2.61 (s, 3H).

Compound 7 (1.56 g, 9.41 mmol) was dissolved in 20 ml of dichloromethane, and phosphorus tribromide (0.85 g, 3.14 mmol) was added. The reaction was run at a low temperature for 3 hours. After the reaction was completed, an appropriate amount of water was added. The resulting mixture was extracted with methylene chloride, dried over anhydrous sodium sulfate, and the organic solvent was evaporated. The resulting material can be directly used without further purification in the next reaction. ESI-MS: [M+H]$^+$ m/z 230.9.

The above resulting material (Compound 8) was dissolved in 20 mL of toluene, and ethylene glycol (0.58 g, 9.41 mmol) and a catalytic amount of p-toluene sulfonic acid were added respectively. The reaction was heated to 80° C. for 3 hours. After the reaction was completed, the toluene was evaporated under reduced pressure, and an appropriate amount of water was added. The resulting mixture was extracted with ethyl acetate, dried over anhydrous sodium sulfate, and the solvent was evaporated to dryness under reduced pressure. The resulting material was separated with column chromatography (ethyl acetate:petroleum ether=1:5) to give Compound 9 as a light yellow solid (1.25 g). ESI-MS: [M+H]$^+$ m/z 272.02. $^1$H-NMR:(300 MHz, CDCl$_3$) δ: 5.96 (s, 1H), 4.56 (s, 2H), 4.20 (m, 4H), 2.64 (s, 3H), 2.63 (s, 3H). $^{13}$C-NMR: 150.07, 149.40, 149.04, 148.07, 103.15, 65.66, 31.15, 20.88, 20.56.

Compound 9 (1.25 g, 4.6 mmol) was dissolved in 20 mL of toluene, and triethyl phosphite (1.52 g, 9.2 mmol) was added. The reaction was heated to 110° C. overnight reaction. After completion of the reaction, methylbenzene was evaporated, and an appropriate amount of water was added. The resulting mixture was extracted with ethyl acetate, dried over anhydrous sodium sulfate, and the solvent was evaporated to dryness under reduced pressure. The resulting material was separated with column chromatography (methanol:dichloromethane 1:10) to give Compound 10 as a pale white solid (1.1 g, 72.9%). ESI-MS: [M+H]$^+$ m/z 331.48. $^1$H-NMR:(300 MHz, CDCl$_3$) δ: 5.99 (s, 1H), 4.27 (m, 4H), 4.11 (m, 4H), 3.76 (d, J=11.1 Hz, 2H), 2.66 (s, 3H), 2.46 (s, 3H), 1.36 (m, 6H).

Compound 10 (1.1 g, 3.3 mmol) was dissolved in 20 mL of dichloromethane, and Compound 3 (0.69 g, 3.3 mmol) and sodium methoxide (0.54 g, 9 g, 64.3. 9 mmol) were added respectively. The reaction was run at room temperature for 2 hours. After the reaction was completed, an appropriate amount of water was added. The resulting mixture was extracted with ethyl acetate, dried over anhydrous sodium sulfate, and the organic solvent was evaporated. The resulting material was separated with column chromatography (ethyl acetate:petroleum ether=1:3) to give Compound 11 as a yellow solid (0.90%). ESI-MS: [M+H]$^+$ m/z 384.18. $^1$H-NMR:(300 MHz, DMSO-d6) δ: 7.95 (s, 2H), 5.83 (s, 2H), 4.18 (m, 4H), 4.02 (m, 4H), 2.63 (s, 6H), 2.59 (s, 6H).

Compound 11 (0.8 g, 1.8 mmol) was dissolved in 20 mL of liquid mixture (Con.HCl:H$_2$O:THF=2:6:7) to be reacted at room temperature for 2 hours. After the reaction was completed, the organic solvent was partially evaporated under reduced pressure, and an appropriate amount of water was added. The resulting mixture was extracted with ethyl acetate, dried over anhydrous sodium sulfate, and the solvent was evaporated to dryness under reduced pressure. The resulting material was separated with column chromatography (ethyl acetate:petroleum ether=1:10) to give Compound 12 as a yellow solid (0.54 g, 87.1%). ESI-MS: [M+H]$^+$ m/z 296.13. $^1$H-NMR:(300 MHz, CDCl$_3$) δ: 10.20 (s, 2H), 8.24 (s, 2H), 2.91 (s, 6H), 2.84 (s, 6H).

Compound 12 (0.54 g, 1.8 mmol) was dissolved in 10 mL of ethanol, and tert-butyl hydroxylamine (0.32 g, 3.55 mmol) was added. The reaction was run at room temperature for 4 hours. After the reaction was completed, the organic solvent was evaporated to dryness under reduced pressure, and an appropriate amount of water was added. The resulting mixture was extracted with ethyl acetate, dried over anhydrous sodium sulfate, and the solvent was evaporated to dryness under reduced pressure. The resulting material was separated with column chromatography (ethyl acetate:petroleum ether=1:10) to give IND-010 as a yellow solid (0.17 g, 22%). ESI-MS: [M+H]$^+$ m/z 439.18. $^1$H-NMR:(300 MHz, CDCl$_3$) δ: 8.06 (s, 2H), 7.87 (s, 2H), 2.73 (s, 6H), 2.58 (s, 6H), 1.67 (s, 18H). $^{13}$C-NMR: 151.97, 148.15, 146.61, 142.77, 129.41, 128.15, 71.53, 28.24, 21.92, 21.08.

Figure 5:
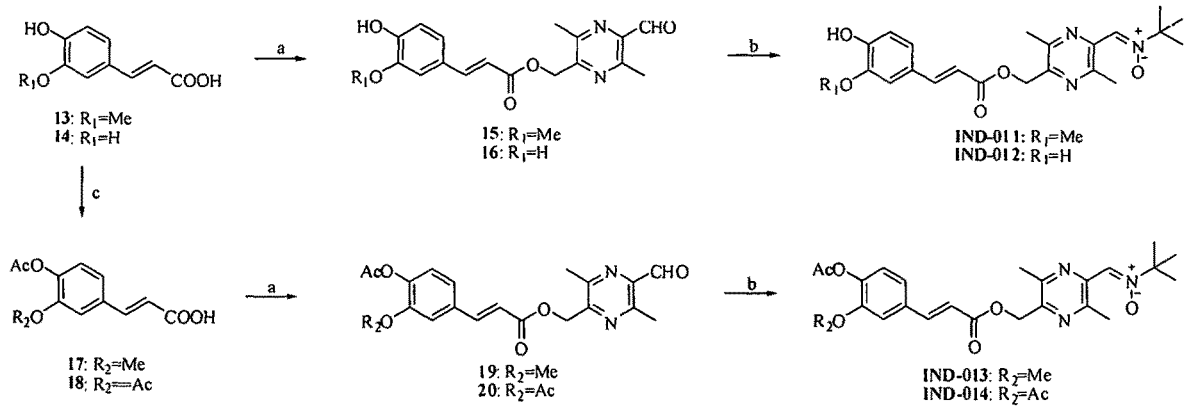
FIG. 5 illustrates the synthesis of the compounds IND-011, IND-012, IND-013 and IND-014.

Example 6. Synthesis of Compound IND-011 (FIG. 5)

Ferulic acid (Compound 13) (0.5 g, 2.6 mmol) was dissolved in 10 ml of N,N-dimethyl formamide, and 5-(bromo methyl)-3,6-dimethyl pyrazine-2-carbaldehyde (Compound 8) (0.53 g, 2.33 mmol) and potassium carbonate (0.58 g, 4.2 mmol) were added respectively. The reaction was run at room temperature for 3 hours. After the reaction was completed, an appropriate amount of water was added. The resulting mixture was extracted with ethyl acetate, dried over anhydrous sodium sulfate, and the solvent was evaporated to dryness under reduced pressure. The resulting material was separated with column chromatography (ethyl acetate:petroleum ether=1:3) to give Compound 15 as a pale white solid (0.39 g, 43.4%). $^1$H-NMR: (300 MHz, CDCl$_3$) δ: 10.34 (s, 1H), 7.64 (d, J=115.9 Hz, 1H), 7.03 (m, 1H), 6.91 (m, 1H), 6.34 (d, J=15.9 Hz, 1H), 5.35 (s, 2H), 3.90 (s, 3H), 2.61 (s, 3H), 2.51 (s, 3H).

Compound 15 (0.39 g, 1.12 mmol) was dissolved in 5 mL of ethanol, and tert-butyl hydroxylamine (0.20 g, 2.24 mmol) was added. The reaction was run at room temperature for 4 hours. After the reaction was completed, an appropriate amount of water was added. The resulting mixture was extracted with ethyl acetate, dried over anhydrous sodium sulfate, and the solvent was evaporated to dryness under reduced pressure. The resulting material was separated with column chromatography (ethyl acetate:petroleum ether=1:1) to give IND-011 as a pale white solid (0.20 g, 43.8%). ESI-MS: [M+H]$^+$ m/z 413.20. $^1$H-NMR: (300 MHz, CDCl$_3$) δ: 7.87 (s, 1H), 7.66 (d, J=15.9 Hz, 1H), 7.13 (m, 2H), 6.92 (d, J=8.2 Hz, 1H), 6.34 (d, J=15.9 Hz, 1H), 5.37 (s, 2H), 3.93 (s, 3H), 2.62 (s, 3H), 2.53 (s, 3H), 1.66 (s, 9H). Anal. (C$_{22}$H$_{27}$N$_3$O$_5$) C, H, C; found C 63.73%, H 6.604%, N 9.99%; requires: C 63.91%, H 6.58%, N 10.16%.

Example 7. Synthesis of Compound IND-012 (FIG. 5)

Caffeic acid (0.47 g, 2.62 mmol) was dissolved in 10 mL of N,N-dimethyl formamide, and 5-(bromo methyl)-3,6-dimethyl pyrazine-2-carbaldehyde (Compound 8) (0.5 g, 2.19 mmol) and sodium bicarbonate (0.28 g, 3.3 mmol) were added respectively. The reaction was run at room temperature for 3 hours. After the reaction was completed, an appropriate amount of water was added. The resulting mixture was extracted with ethyl acetate, dried over anhydrous sodium sulfate, and the solvent was evaporated to dryness under reduced pressure. The resulting material was separated with column chromatography (ethyl acetate:petroleum ether=1:1) to give Compound 16 as a pale white solid (0.62 g, 72%). ESI-MS: [M+H]$^+$ m/z 329.16. $^1$H-NMR:(300 MHz, CDCl$_3$) δ: 10.18 (s, 1H), 7.54 (d, J=15.9 Hz, 1H), 7.00 (d, J=1.6 Hz, 1H), 6.89 (dd, J=8.2, 1.7 Hz, 1H), 6.81 (d, J=8.2 Hz, 1H), 6.20 (d, J=15.9 Hz, 1H), 5.39 (s, 2H), 2.83 (s, 3H), 2.70 (s, 3H). $^{13}$C-NMR: 194.48, 166.62, 152.25, 150.98, 150.23, 149.08, 146.53, 146.04, 143.06, 125.85, 122.09, 116.17, 115.42, 113.56, 64.18, 28.07, 21.65, 20.69. Anal. (C$_{17}$H$_{16}$N$_2$O$_5$) C, H, C; found C 61.87%, H 4.98%, N 8.33%; requires: C 62.19%, H 4.91%, N 8.53%.

Compound 16 (0.45 g, 1.37 mmol) was dissolved in 5 mL of ethanol, and tert-butyl hydroxylamine (0.24 g, 2.74 mmol) was added. The reaction was run at room temperature for 4 hours. After the reaction was completed, an appropriate amount of water was added. The resulting mixture was extracted with ethyl acetate, dried over anhydrous sodium sulfate, and the solvent was evaporated to dryness under reduced pressure. The resulting material was separated with column chromatography (ethyl acetate:petroleum ether=1:1) to give IND-012 as a pale white solid (0.45 g, 44.8%). ESI-MS: [M+H]$^+$ m/z 400.20. $^1$H-NMR: (300 MHz, DMSO-d6) δ: 8.05 (s, 1H), 7.53 (d, J=15.9 Hz, 1H), 7.07 (d, J=2.1 Hz, 1H), 7.04 (dd, J=8.1, 1.8 Hz, 1H), 6.75 (d, J=8.1 Hz, 1H), 6.34 (d, J=15.9 Hz, 1H), 5.32 (s, 2H), 2.53 (s, 3H), 2.35 (s, 3H), 1.53 (s, 9H). $^{13}$C-NMR: 166.69, 150.01, 149.09, 148.80, 147.65, 146.36, 146.06, 144.18, 128.30, 125.87, 122.08, 116.18, 115.39, 113.69, 71.10, 64.65, 28.07, 21.20, 20.52. Anal. (C$_{21}$H$_{25}$N$_3$O$_5$·H$_2$O) C, H, C; found C 60.55%, H 6.521%, N 9.59%; requires: C 60.42%, H 6.52%, N 10.07%.

Example 8. Synthesis of Compound IND-013 (FIG. 5)

Ferulic acid (2 g, 10.3 mmol) was dissolved in 30 mL of acetic anhydride, and a catalytic amount of dimethylaminopyridine was added. The reaction was run at room temperature overnight. After the reaction was completed, 20 ml of water was added. The reaction was stirred at room temperature for 1 hour, and then extracted with ethyl acetate, dried over anhydrous sodium sulfate, and the solvent was evaporated to dryness under reduced pressure. The resulting material can be used directly in the next step without further purification.

(E)-3-(4-Acetoxy-3-methoxyphenyl) acrylic acid (Compound 17) (0.37 g, 1.58 mmol) was dissolved in 20 mL of N,N-dimethylformamide, and Compound 8 (0.3 g, 1.31 mmol) and potassium carbonate (0.28 g, 2.0 mmol) were added respectively. The reaction was run at room temperature for 3 hours. After the reaction was completed, an appropriate amount of water was added. The resulting mixture was extracted with ethyl acetate, dried over anhydrous sodium sulfate and the solvent was evaporated to dryness under reduced pressure. The resulting material was separated with column chromatography (ethyl acetate:petroleum ether=1:3) to give Compound 19 as a pale white solid (0.26 g, 52.8%). ESI-MS: [M+H]$^+$ m/z 385.00. $^1$H-NMR: (300 MHz, CDCl$_3$) δ: 10.10 (s, 1H), 7.72 (d, J=16.0 Hz, 1H), 7.56 (d, J=1.7 Hz, 1H), 7.33 (dd, J=8.2, 1.7 Hz, 1H), 7.14 (d, J=8.1 Hz, 1H), 6.84 (d, J=16.0 Hz, 1H), 5.46 (s, 2H), 3.82 (s, 3H), 2.71 (s, 3H), 2.65 (s, 3H), 2.27 (s, 3H). $^{13}$C-NMR: 194.46, 168.84, 166.31, 152.02, 151.65, 151.00, 150.24, 145.26, 143.15, 141.62, 133.39, 123.71, 122.33, 118.11, 112.48, 64.40, 56.49, 21.63, 20.88, 20.67. Anal. (C$_{20}$H$_{20}$N$_2$O$_6$) C, H, C; found C 62.88%, H 5.273%, N 7.27%; requires: C 62.49%, H 5.24%, N 7.29%.

Compound 19 (0.26 g, 0.68 mmol) was dissolved in 5 mL of ethanol, and tert-butylhydroxylamine (0.12 g, 1.36 mmol) was added. The reaction was run at room temperature for 4 hours. After the reaction was completed, an appropriate amount of water was added. The resulting mixture was extracted with ethyl acetate, dried over anhydrous sodium sulfate and the solvent was evaporated to dryness under reduced pressure. The resulting material was separated with column chromatography (ethyl acetate:petroleum ether=1:1) to give IND-013 as a pale white solid (0.10 g, 33%). ESI-MS: [M+H]$^+$ m/z 455.21. $^1$H-NMR:(300 MHz, CDCl$_3$) δ: 7.86 (s, 1H), 7.67 (s, J=15.9 Hz, 1H), 7.12 (m, 2H), 7.06 (d, J=8.0 Hz, 1H), 6.44 (d, J=16.0 Hz, 1H), 5.37 (s, 2H), 3.87 (s, 3H), 2.62 (s, 3H), 2.53 (s, 3H), 2.33 (s, 3H), 1.65 (s, 9H). $^{13}$C-NMR: 168.74, 166.27, 151.39, 150.30, 148.90, 147.23, 144.98, 143.64, 141.56, 133.19, 127.81, 123.29, 121.30, 117.46, 111.30, 71.55, 65.06, 55.93, 28.19, 21.54, 20.67, 20.60. Anal. (C$_{24}$H$_{29}$N$_3$O$_6$) C, H, C; found C 62.94%, H 6.314%, N 9.22%; requires: C 63.28%, H 6.42%, N 9.23%.

Example 9. Synthesis of Compound IND-014 (FIG. 5)

Caffeic acid (2 g, 11.1 mmol) was dissolved in 30 mL of acetic anhydride, and a catalytic amount of dimethylaminopyridine was added. The reaction was run at room temperature overnight. After the reaction was completed, adding 20 ml of water. The reaction was stirred at room temperature for 1 hour, and then extracted with ethyl acetate, dried over anhydrous sodium sulfate, and the solvent was evaporated to dryness under reduced pressure. The resulting material was can be used directly to the next step without further purification.

(E)-3-(3,4-Acetoxyl phenyl) acrylic acid (Compound 18) (1.1 g, 4.15 mmol) was dissolved in 20 mL of N,N-dimethylformamide, and Compound 8 (0.95 g, 4.15 mmol) and potassium carbonate (1.14 g, 8.30 mmol) were added respectively. The reaction was run at room temperature for 3 hours. After the reaction was completed, an appropriate amount of water was added. The resulting mixture was extracted with ethyl acetate, dried over anhydrous sodium sulfate, and the solvent was evaporated to dryness under reduced pressure. The resulting material was separated with column chromatography (ethyl acetate:petroleum ether=1:2) to give Compound 20 as a pale white solid (0.8 g, 47%). ESI-MS: [M+H]$^+$ m/z 413.15. $^1$H-NMR:(300 MHz, CDCl$_3$) δ: 10.20 (s, 1H), 8.02 (s, 1H), 7.70 (d, J=16.0 Hz, 1H), 7.42 (dd, J=8.4, 2 Hz, 1H), 7.38 (d, J=2.0 Hz, 1H), 7.24 (d, J=8.4 Hz, 1H), 6.48 (d, J=16.0 Hz, 1H), 5.42 (s, 2H), 2.97 (s, 3H), 2.89 (s, 3H), 2.85 (s, 3H), 2.70 (s, 3H), 2.31 (d, J=1.0 Hz, 6H).

Compound 20 (0.45 g, 1.09 mmol) was dissolved in 5 mL of ethanol, and tert-butyl hydroxylamine (0.98 g, 1.09 mmol) was added. The reaction was run at room temperature for 4 hours. After the reaction was completed, an appropriate amount of water was added. The resulting mixture was extracted with ethyl acetate, and dried over anhydrous sodium sulfate, and the solvent was evaporated to dryness under reduced pressure. The resulting material was separated with column chromatography (ethyl acetate:petroleum ether=1:1) to give IND-014 as a pale white solid (0.45 g, 85%). ESI-MS: [M+H]$^+$ m/z 484.08. $^1$H-NMR: (300 MHz, CDCl$_3$) δ: 7.85 (s, 1H), 7.64 (d, J=15.9 Hz, 1H), 7.39 (dd, J=8.4, 1.8 Hz, 1H), 7.35 (d, J=1.5 Hz, 1H), 6.21 (d, J=8.4 Hz, 1H), 6.42 (d, J=15.9 Hz, 1H), 5.35 (s, 2H), 2.53 (s, 314), 2.50 (s, 3H), 2.29 (s, 6H), 1.63 (s, 9H). $^{13}$C-NMR: 168.05, 167.95, 166.03, 150.75, 148.86, 147.17, 143.75, 143.65, 143.58, 142.44, 133.06, 127.88, 126.51, 123.97, 122.84, 118.39, 71.54, 65.08, 28.16, 21.50, 20.66, 20.60, 20.55. Anal. ($C_{25}H_{29}N_3O_7$) C, H, C; found C 62.37%, H 6.086%, N 8.71%; requires: C 62.10%, H 6.05%, N 8.69%.

Figure 6:
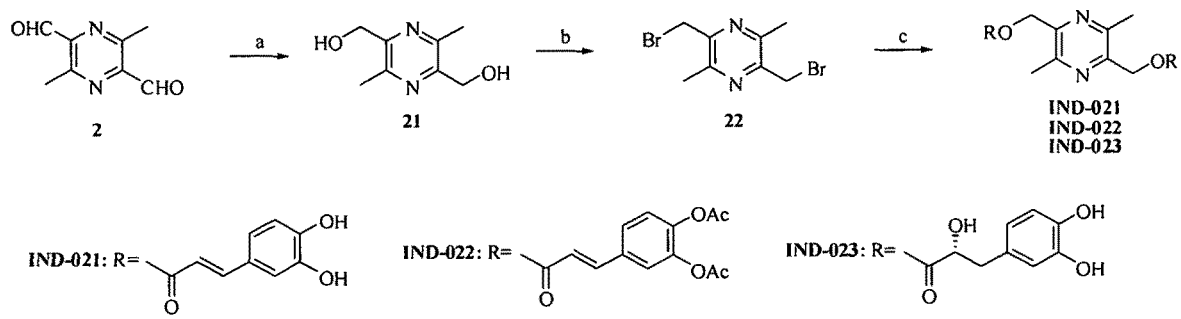
FIG. 6 illustrates the synthesis of the compounds IND-021, IND-022 and IND-023.

Example 10. Synthesis of Compound IND-021
(FIG. 6)

3,6-Dimethyl pyrazine-2,5-dimethyl formaldehyde (compound 2) (5 g, 30.5 mmol) was dissolved in 50 ml of 1,2-dichloroethane, and sodium borohydride (2.3 g, 60.1 mmol) was added in batches. The reaction was run at room temperature overnight. After reaction was completed, the reaction was filtered. To the filtrate was added an appropriate amount of silica gel, and the solvent was evaporated to dryness under reduced pressure. The resulting material was separated with column chromatography (ethyl acetate:petroleum ether=1:3), to give Compound 21 as a light yellow solid (3.1 g, 60.8%). ESI-MS: [M+H]$^+$ m/z 169.1. $^1$H-NMR: (300 MHz, CDCl$_3$) δ: 4.73 (d, J=4.2 Hz, 4H), 4.25 (m, 2H), 2.47 (s, 6H).

Compound 21 (1.86 g, 5.6 mmol) was dissolved in 10 mL of dichloromethane, and phosphorus tribromide (1.5 g, 5.6 mmol) was added. The reaction was run at a low temperature for 3 hours. After the reaction was completed, an appropriate amount of water was added. The resulting mixture was extracted with dichloromethane, and dried over anhydrous sodium sulfate, and the organic solvent was evaporated. The resulting material was separated with column chromatography (ethyl acetate:petroleum ether=1:15), to give Compound 22 as a light yellow solid (54.5%) 1.8 g. ESI-MS: [M+H]$^+$ m/z 394.80. $^1$H-NMR: (300 MHz, CDCl$_3$) δ: 4.55 (s, 4H), 2.42 (s, 6H).

Caffeic acid (0.12 g, 0.68 mmol) was dissolved in 5 mL of N,N-dimethylformamide, and NaHCO$_3$ (54 mg, 0.68 mmol) was added, and the reaction was stirred at room temperature for 15 min. Compound 22 (0.10 g, 0.34 mmol) was added, and the reaction was stirred at room temperature for 48 hours. After the reaction was completed, an appropriate amount of water was added, extracted with ethyl acetate, and dried over anhydrous sodium sulfate, and the solvent was evaporated to dryness under reduced pressure. The resulting material was separated by column chromatography (dichloromethane/methanol=15:1) to give IND-021 as a white solid (58 mg, 34%). ESI-MS: [M+H]$^+$ m/z 493.03. $^1$H-NMR:(300 MHz, DMSO-d6) δ: 9.60 (s, 2H), 9.12 (s, 2H), 7.53 (d, J=15.9 Hz, 2H), 7.07 (d, J=1.8 Hz, 2H), 7.01 (dd, J=8.1, 2.1 Hz, 2H), 6.76 (d, J=8.1 Hz, 2H), 6.34 (d, J=15.9 Hz, 2H), 5.31 (s, 4H), 2.52 (s, 6H). $^{13}$C-NMR: 166.69, 149.33, 149.03, 147.95, 146.34, 146.03, 125.90, 122.05, 116.18, 115.43, 113.73, 64.60, 20.71. Anal. ($C_{16}H_{20}N_4O_2$) C, H, C; found C 64.16%, H 7.019%, N 18.56%; requires: C 63.98%, H 6.71%, N 18.65%.

Example 11. Synthesis of Compound IND-022
(FIG. 6)

(E)-3-(3,4-Diacetoxyphenyl) acrylic acid (0.18 g, 0.64 mmol) was dissolved in 5 mL of N,N-dimethylformamide, and NaHCO3 (63 mg, 0.75 mmol) was added, The reaction was stirred at room temperature for 15 min. Compound 22 (0.10 g; 0.34 mmol) was added, and the reaction was stirred overnight at room temperature. After the reaction was completed, an appropriate amount of water was added, extracted with ethyl acetate, and dried over anhydrous sodium sulfate, and the solvent was evaporated to dryness under reduced pressure. The resulting material was separated by column chromatography (ethyl acetate:petroleum ether=1:1) to give IND-026 as a white solid (60 mg, 32%). ESI-MS: [M+H]$^+$ m/z 660.98. $^1$H-NMR:(300 MHz, CDCl$_3$) δ: 7.69 (d, J=15.9 Hz, 2H), 7.42 (dd, J=8.4, 1.8 Hz, 2H), 7.37 (d, J=1.8 Hz, 2H), 7.24 (d, J=8.4 Hz, 2H), 6.45 (d, J=15.9 Hz, 2H), 5.38 (s, 4H), 2.63 (s, 6H), 2.3 (d, J=1.2 Hz, 12H). $^{13}$C-NMR: 168.14, 168.05, 166.13, 149.67, 147.48, 143.81, 143.65, 142.44, 133.08, 126.55, 124.02, 122.88, 118.38, 65.01, 20.72, 20.72. Anal. ($C_{34}H_{32}N_2O_{12}.0.5H_2O$) C, H, C; found C 60.97%, H 5.076%, N 4.01%; requires: C 60.98%, H 4.97%, N 4.18%.

Example 12. Synthesis of Compound IND-023
(FIG. 6)

Sodium danshensu (9 g, 41.1 mmol) was added to 40 mL of N,N-dimethylformamide with stirring. Compound 22 (4 g, 13.7 mmol) was then added and reacted at room temperature for 2 hours. After the reaction was completed, 100 mL of water was added and the mixture was extracted with ethyl acetate (200 mL×3). The organic layers were combined, washed twice with saturated sodium chloride (150 mL×2), and concentrated under reduced pressure. The residue was purified by silica gel column chromatography (CH2Cl2:CH3OH=15:1) to give IND-023 as a white solid (2.0 g, 28%). $^1$H-NMR:(300 MHz, DMSO-d6) δ: 8.69 (s, 4H), 6.64-6.53 (m, 4H), 6.42 (dd, J=8.0, 2.0 Hz, 2H), 5.56 (d, J=6.1 Hz, 2H), 5.20 (s, 4H), 4.20 (dt, J=7.6, 5.4 Hz, 2H), 2.82 (dd, J=13.8, 5.1 Hz, 2H), 2.67 (dd, J=13.8, 7.8 Hz, 2H), 2.43 (s, 3H). $^{13}$C-NMR: 173.76, 149.43, 147.58, 145.22, 144.16, 128.67, 120.45, 117.22, 115.66, 72.13, 64.75, 20.49.

Figure 7:
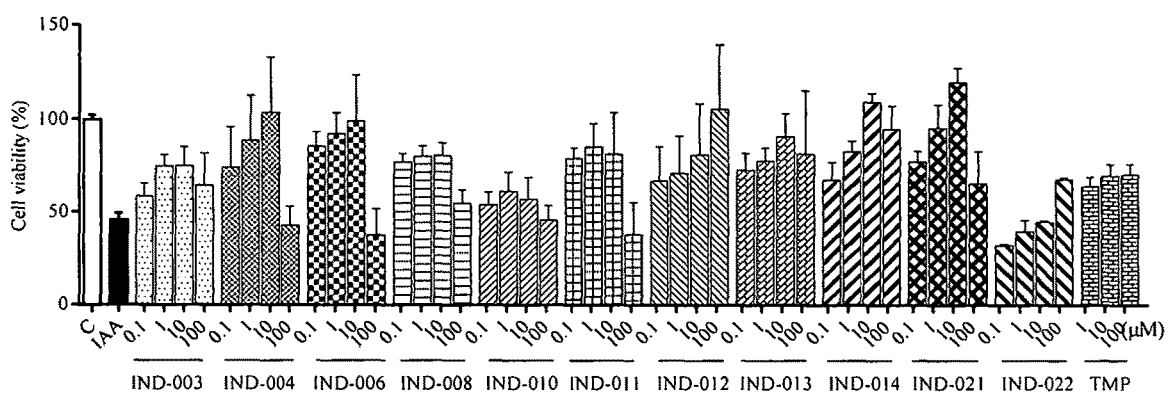
FIG. 7 shows the protective effect of the pyrazine derivative on IAA-induced PC12 cell damage.

Example 13. Protective Effect of Pyrazine Derivatives on IAA-induced PC12 Cell Damage
(FIG. 7)

PC12 cells were seeded in a 96-well plate and incubated at 37° C. in a 5% CO$_2$ incubator for 24 hours, then 100 μL of IAA (30 μM) was added for induction for 2 hours. The medium was aspirated and each of the compounds was added to be incubated for 24 hours. After incubation, to each well was added 11.1 μL of MTT. After 4 hours, the absorbance was measured at 570 nm with a microplate reader. The results as shown in the figure indicate that the pyrazin derivatives have a significant protective effect on IAA-induced PC12 cell damage.

Figure 8:
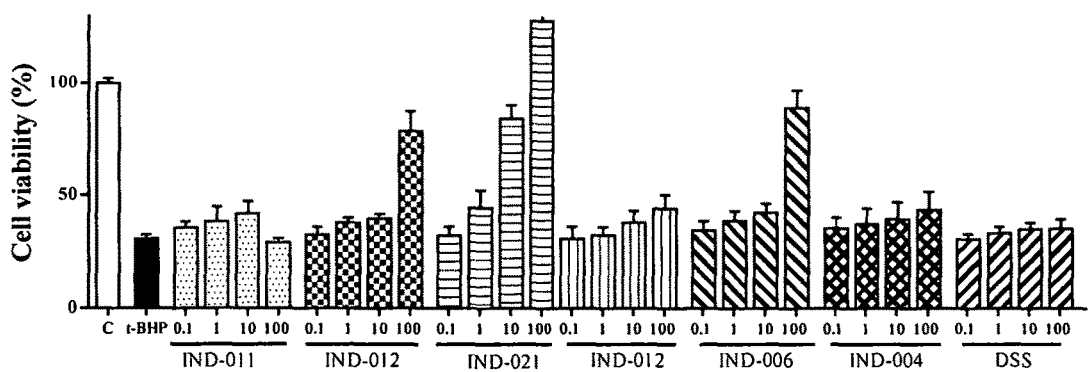
FIG. 8 shows the protective effect of the pyrazine derivative on t-BHP-induced H9c2 cell damage.

Example 14. Protective Effect of Pyrazine Derivatives on t-BHP-Induced H9c2 Cell Damage
(FIG. 8)

H9c2 cells were seeded in a 96-well cell culture plate at a density of 1×10$^4$/well, and cultured in DMEM complete medium for 24 hours. Then, t-BHP was diluted with serum-free DMEM to replace the initial culture medium in the culture plate. The culture process was further carried out for 12 hours, and then 11.1 μL of MTT (5 mg/mL) was added and the process was carried out for additional 4 hours. The medium was aspirated and in each well was added 100 μL of DMSO. The solution was shaken evenly on a shaking table, and the absorbance value was measured at a wavelength of 570 nm with a BioTek microplate reader to calculate the cell viability. After 4 hours. The t-BHP concentration corresponding to about 50% cell mortality rate of the blank group was used as the cell modeling concentration for subsequent experiment.

Figure 9:
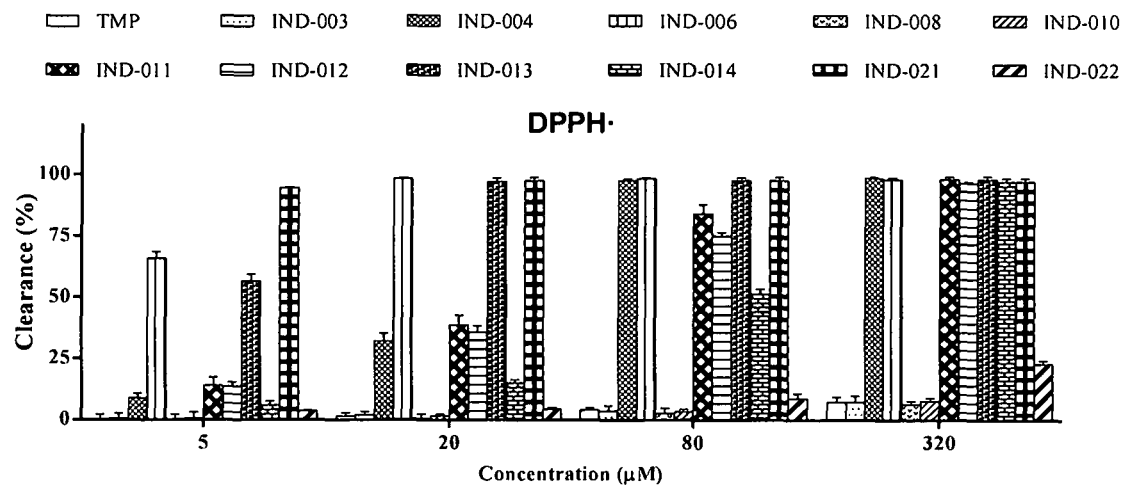
FIG. 9 shows the ability of the pyrazine derivative to scavenge DPPH.

Example 15. Clearance Capacity of Pyrazine Derivatives for DPPH. (FIG. 9)

In a 96-well plate was added a 100 µl solution of each samples in different concentrations (sample group) or 100 µl of methanol (blank control), and 100 µL of DPPH solution in methanol (final concentration of 50 µm) was added rapidly. Three duplicated wells were set for each sample concentration. The solution was shaken evenly at room temperature for 1 hour, and the absorbance value was measured at a wavelength of 517 nm with a microplate reader. The DPPH clearance rate was calculated based on the following formula:

Clearance (%)=$(A_{ctrl}-A_{sample})/(A_{sample}) \times 100$.

Figure 10:
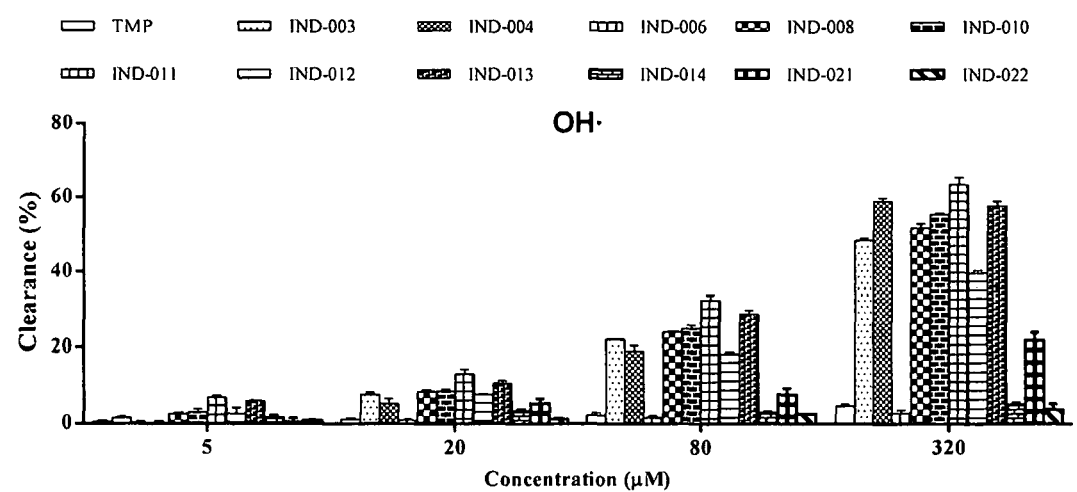
FIG. 10 shows the ability of the pyrazine derivative to scavenge hydroxyl radicals (.OH)

Example 16. Cleavage Capacity of Hydroxy Radicals (.OH) of Pyrazine Derivatives (FIG. 10)

In a 48-well plate was added sequentially 50 µl of 1.0 mM of p-NDA, and 300 µl of $H_2O$ (control group) or 300 µl of sample solution (sample group). Then, 125 µL of 1.0 mM $H_2O_2$ and 125 L of 2.0 mM FeSO4 were added separately with two dispensers on a Biotek microplate reader with a total volume of 600 µL. After shaking, the absorbance of the reaction system in well mode was measured at 440 nm wavelength within 100 s, and the hydroxyl radical clearance rate was calculated based on the following formula:

Clearance (%)=$[1-(A_0-A_t)/A_0] \times 100$.

Figure 11:
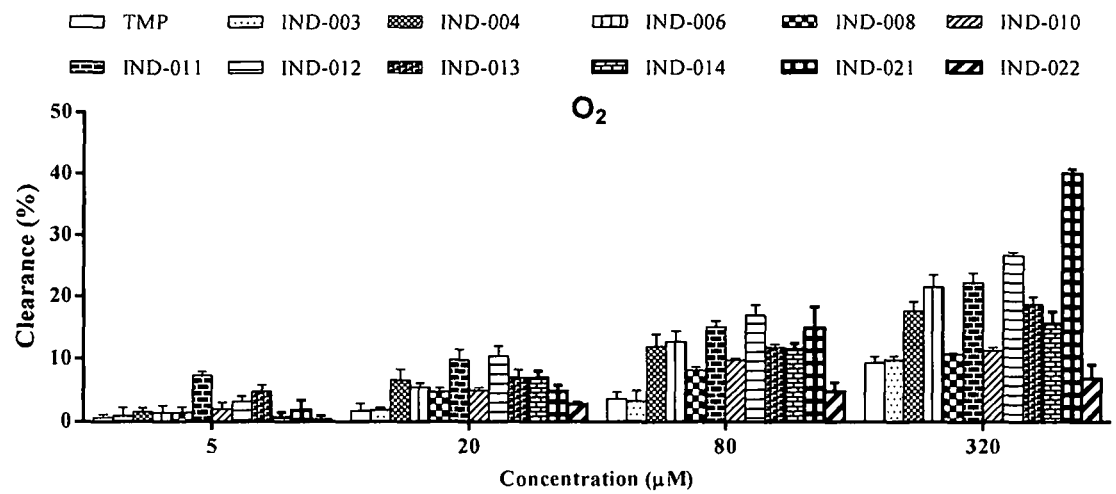
FIG. 11 shows the ability of the pyrazine derivative to scavenge superoxide anion ($O_2.^-$)

Example 17, Clearance Capacity of Pyrazine Derivatives for Superoxide Anions ($O_2.^-$) (FIG. 11)

In a 48-well plate was added sequentially 250 µL of 50 mM Tris-HCl, and 300 µL of $H_2O$ (control group) or 300 µL of sample solution (sample group). Then, 50 µL of 2.0 mM pyrogallol was added with a dispenser on a Biotek microplate reader with a total volume of 600 µL. After shaking, the absorbance of the reaction system in well mode was measured at 320 nm wavelength in every 30 s for 300 s. With various of absorbance values, The clearance rate of superoxide anions in the sample was calculated based on the following formula:

Clearance (%)=$[1-(dA/dt-dA_t/dt)/dA/dt] \times 100$.

Figure 12:
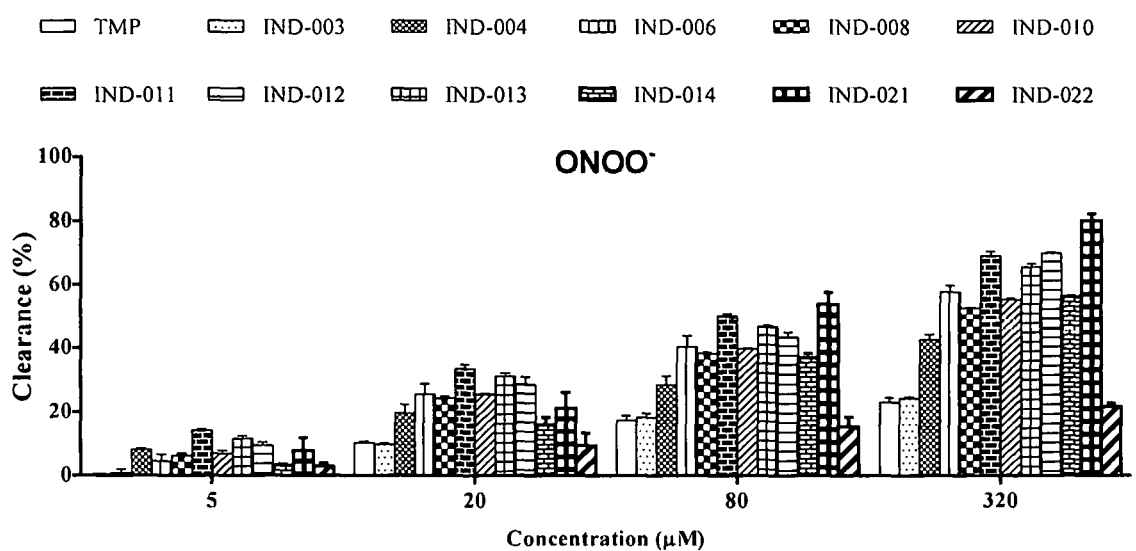
FIG. 12 shows the ability of the pyrazine derivative to scavenge peroxynitrite ($ONOO^-$)

Example 18. Clearance Capacity of Pyrazine Derivatives to Peroxynitrite ($ONOO^-$) (FIG. 12)

In photometric tubes were added sequentially 150 µL of PBS, 250 µL of PBS (blant group) or a sample solution in different concentrations, and finally 50 µL of 1.0 mM Luminol solution and 3 mg/mL of SIN-µL solution to stimulate the reaction, with a total volume of 500 µL. At 37° C., the luminous value was recorded in every 100 s for 2000 s. The clearance rate was calculated based on the following formula:

Clearance (%)=$(A_{ctrl}-A_{sample})/A_{sample} \times 100$.

Figure 13:
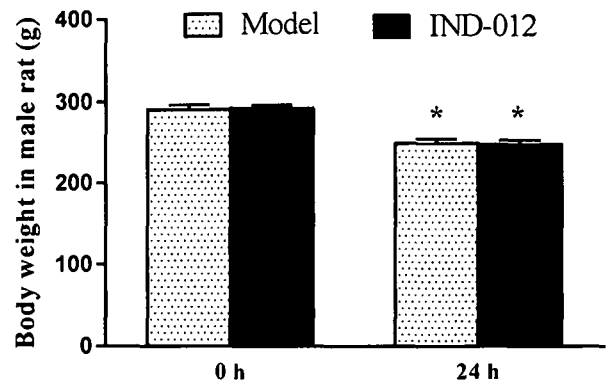
FIG. 13 shows the effect of IND-012 on pre- and postoperative body weight in a rat model of permanent cerebral ischemia.
Figure 14:
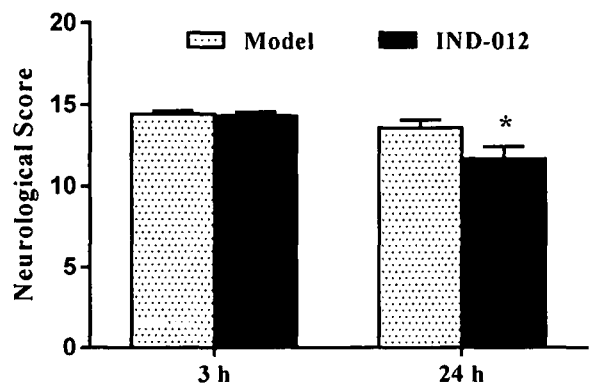
FIG. 14 shows behavioral improvement of IND-012 in a rat model of permanent cerebral ischemia.
Figure 15:
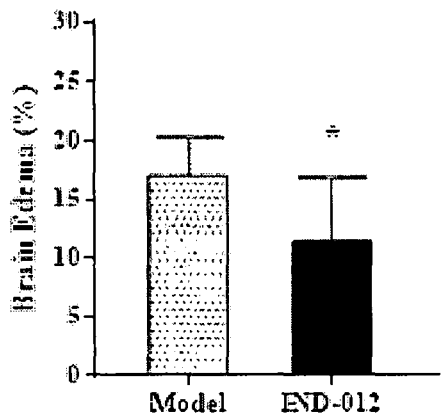
FIG. 15 shows the effect of IND-012 on the level of cerebral edema in a rat model of permanent cerebral ischemia.

Example 19. Protective Effect of Pyrazine Derivative IND-012 in a Permanent Brain Ischemic Model of SD Rats (FIGS. 13-15)

A SD rat was inhaled with 2.5% isoflurane for anesthesia and was then fixed. An incision was made in the middle of the neck, and the right common carotid artery and external carotid artery were exposed first. The end close to heart of the common carotid artery and the external carotid artery were separately ligated. The carotid embedded thread plug was carefully inserted from the internal carotid artery into the internal carotid artery until reaching the starting portion of the middle cerebral artery with the insertion depth of 17-18 mm. After insertion of the thread plug, the change of the local blood flow in the brain was measured with a flow meter. The standard for a successful model was set when the blood flow volume after the embolization was reduced by more than 60% from the base value. Throughout the experiment, the rat was placed on a 37° C. thermostatic table, and the rat after waking up was placed into the original cage for continue feeding. IND-012 was intraperitoneally injected at 3 hour and 6 hour respectively after middle cerebral artery occlusion, in a dosage of 30 mg/kg and with a solvent of 15% ethanol+45% propylene glycol+40% saline. After 24 hours of modeling, anesthesia was performed with pentobarbital sodium, and the brain was decapitated to obtain brain slices (7 slices per brain tissue and 2 mm in thickness for each slice), which were stained with TTC for calculating the size of infarct and area of cerebral edema, respectively. Animal weight was measured before and 24 h after surgery, and the changes in body weight were recorded.

Figure 16:
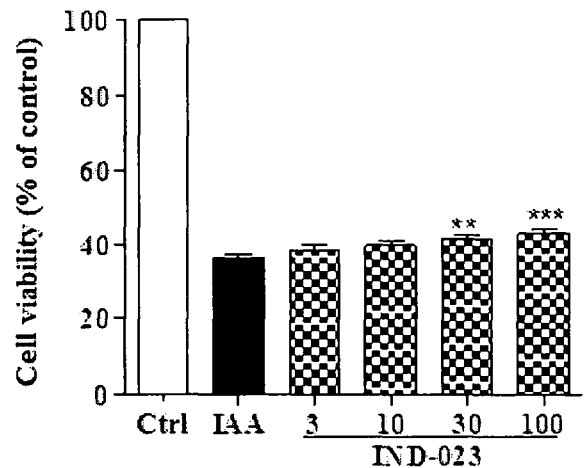
FIG. 16 shows the protective effect of IND-023 on IAA-induced H9c2 cell injury.

Example 21. Protective Effect of Compound IND-023 on IAA-Induced H9c2 Cell Damage (FIG. 16)

H9c2 cells were seeded in a 96-well plate and incubated for 24 hours at 37° C. in a 5% $CO_2$ incubator. Then, 100 µL it of IND-023 in different concentrations was added and subjected to prepreparation for 1 hour. After induction with IAA (50 µM) for 4 hours, MTT was added, and the absorbance was measured at 490 nm with a microplate reader. The results, as shown in the figure, indicate that IND-023 has a significant protective effect on IAA-induced H9c2 cell injury.

Figure 17:
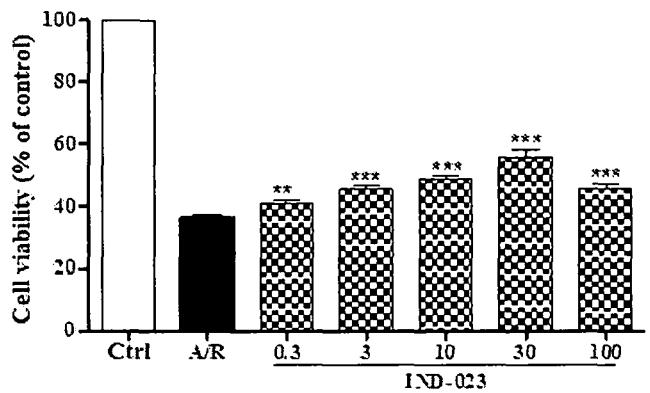
FIG. 17 shows the protective effect of IND-023 on A/R-induced H9c2 cell injury.

Example 22, Protective Effect of Compound IND-023 on A/R-Induced H9c2 Cell Damage (FIG. 17)

H9c2 cells were seeded in a 96-well plate and incubated at 37° C. in a 5% $CO_2$ incubator for 24 hours, and then hypoxia was indicated. IND-023 of the drug group was diluted with KRB buffer as an anoxic solution into desired concentrations. The model group, after added only KRB solution with 50 µL in each well, was placed into the hypoxic box to be incubated for 12 hours, whereas, the blank group, after the initial medium was replaced with serum-free high glucose DMEM, was placed into a normal incubator. After the end of hypoxia, the medium of the model group was changed to serum-free high glucose DMEM. The drug group was diluted with high-glucose DMEM to corresponding concentrations with 100 µL each well, and was placed in a normal incubator and cultured for 4 hours. After the end of reoxygenation, the existing medium was removed and MTT was added. After 4 hours, the OD value was measured at 490 nm to calculate cell viability. The results, as shown in the figure, indicate that IND-023 has a significant protective effect on A/R-induced H9c2 cell injury.

Figure 18:
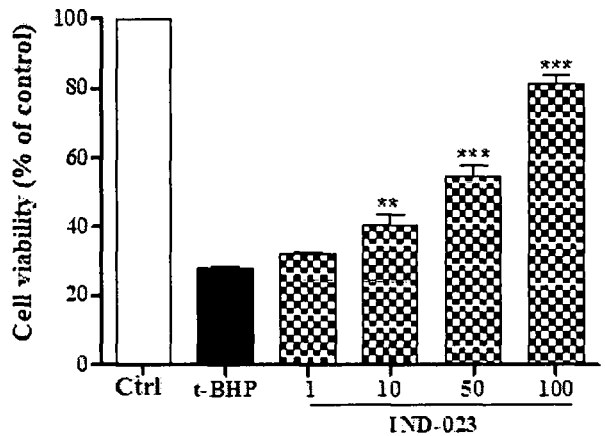
FIG. 18 shows the protective effect of IND-023 on t-BHP-induced H9c2 cell injury.

Example 23. Protective Effect of Compound IND-023 on t-BHP-Induced H9c2 Cell Injury (FIG. 18)

H9c2 cells were seeded in a 96-well plate in a density of $1 \times 10^4$ cells/well, and cultured in a DMEM complete medium for 24 hours. IND-023 was pre-protected for 1 hour, and then diluted t-BHP 150 μM with serum-free high glucose DMEM and induced for 12 hours. MTT (5 mg/mL) was added and cultured for 4 hours. Then, the medium was aspirated, and 100 μL, of DMSO was added to each well. The cells were homogenized by shaking in a shaking table and the absorbance was measured at a wavelength of 490 nm with a BioTek microplate reader to calculate the cell viability. The results, as shown in the figure, indicate that IND-023 has a significant protective effect on t-BHP-induced H9c2 cell injury.

Figure 19:
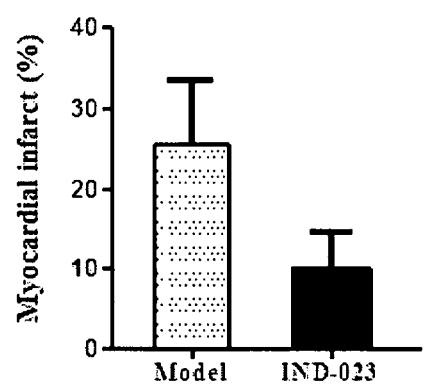
FIG. 19 shows the protective effect of IND-023 on SD rat myocardial infarction model.

Example 20. Protective Effect of Compound IND-023 in SD Rat Myocardial Infarction Model (FIG. 19)

A male SD rat was anesthetized with 2.5% isoflurane and fixed. Tracheotomy was performed, and the rat was connected to a ventilator and was cut at the position 0.5 cm on the left side of the sternal along the 2nd intercostal space and the 4th intercostal space 4. The subcutaneous tissue and muscle were bluntly dissected, and the chest was opened at the 4th intercostal space with forceps to expose the chest. The pericardium was carefully opened. The anterior descending branch of the left coronary artery was ligated with non-invasive suture needle No. 8 at the position of 2 to 3 mm from the lower edge of the left atrial appendage. The elevation of the ST segment of lead II ECG after the ligation was taken as an indication of a successful model. Throughout the experiment process, the rat was placed and kept warm on a 37° C. thermostatic table, and after waking up, the rat was placed into the original cage to continue feeding. After successful modeling, the rat was injected via tail vein for 15 min to give 20 mg/kg of IND-023 with a solution of 5% ethanol+5% polyethylene glycol+90% normal saline. Then, 24 hours after the modeling, the rat was anesthetized by inhaling isoflurane and given by tail vein injection with 2 ml 1% TTC dye, and 3 min later, thoracotomy was performed to take out the heart, and the right atrium, right ventricle and left atrial appendage were removed to be placed in frozen at −20° C. for 10 min. The entire left ventricle and the myocardial tissue of the left ventricular myocardial infarction were weighted respectively. Myocardial infarction is indicated as: (Weight of the myocardial tissue of the left ventricular myocardial infarction)/(Weight of the left ventricle mass)*100.

While certain specific embodiments have been described in detail, many details have been set forth for purposes of illustration and are not intended to limit the scope of the claims attached hereafter. It should be understood that the invention is susceptible to additional embodiments and that certain of the details described herein may be varied considerably with different substitutions, changes and modifications without deviating from the basic principles of the invention defined by the claims attached herein and their equivalents.

The invention claimed is:

1. A pyrazine derivative of formula II:

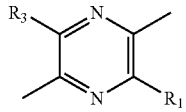

II or pharmaceutically acceptable salts thereof, wherein:

$R_1$ is a group selected from R'COOCH(R"), R'CH═CH, R'CONH, R'CONH(R"), wherein R' and R" are each a saturated or unsaturated alkyl, cycloalkyl, substituted or unsubstituted aryl or heteroaryl;

$R_3$ is nitronyl;

wherein, the alkyl is a C1-C10 alkyl, the cycloalkyl is a five-membered or six-membered cycloalkyl, the aryl is a single-ring aryl, the heteroaryl is a single-ring heteroaryl; the substitution group is $NH_2$, $NO_2$, $N(CH_3)_2$, $ONO_2$, F, Cl, Br, I, OH, $OCH_3$, $CO_2H$, $CO_2CH_3$, CN, aryl, or nitronyl.

2. The pyrazine derivative or a pharmaceutically acceptable salt thereof according to claim 1, wherein $R_3$ is HC═N$^+$(O$^-$)tBu, such that the pyrazine derivative has formula IV:

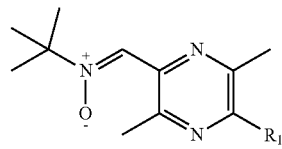

IV wherein:

$R_1$ is a group selected from R'COOCH(R"), R'CH═CH, R'CONH, R'CONH(R"), wherein R' and R" are each a saturated or unsaturated alkyl, cycloalkyl, substituted or unsubstituted aryl or heteroaryl.

3. The pyrazine derivative or a pharmaceutically acceptable salt thereof according to claim 2, wherein the pyrazine derivative has one of structures below:

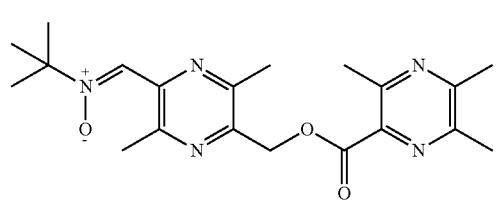

IND-007

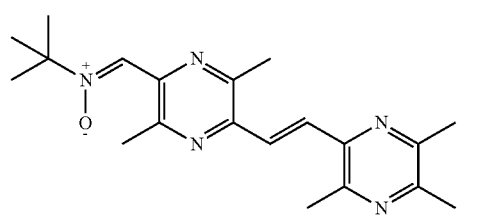

IND-008

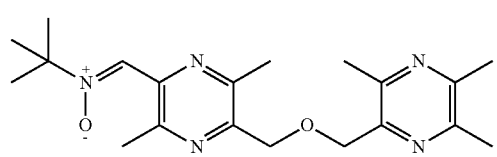

IND-009

IND-010
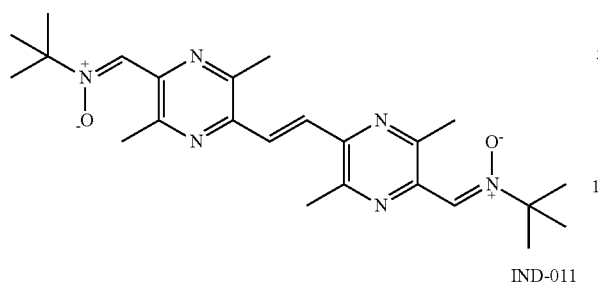

IND-011
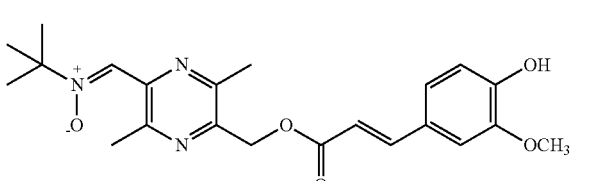

IND-012
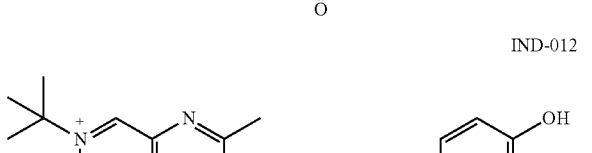

IND-013
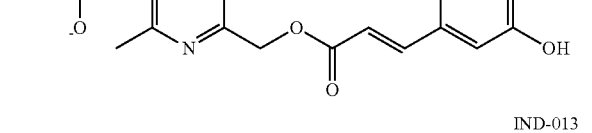

IND-014
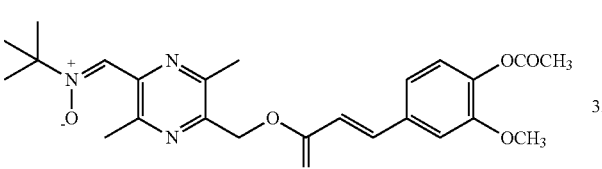

IND-015
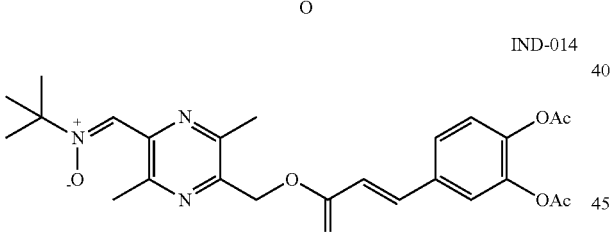

IND-016
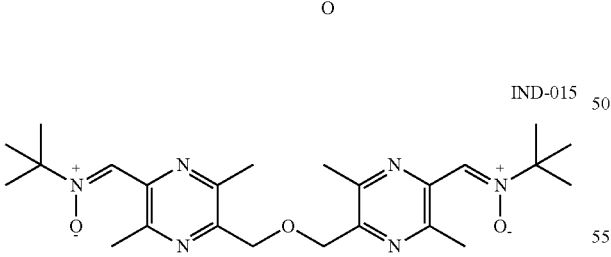

IND-017
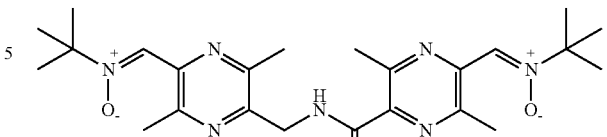

IND019
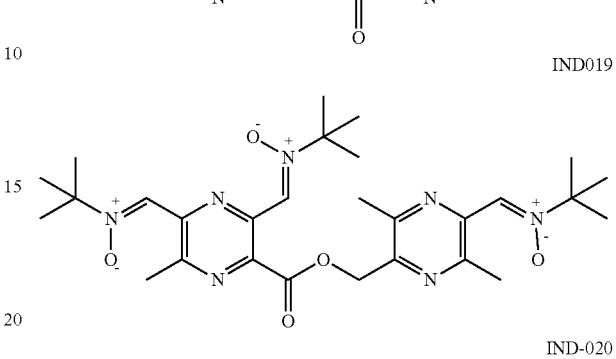

IND-020
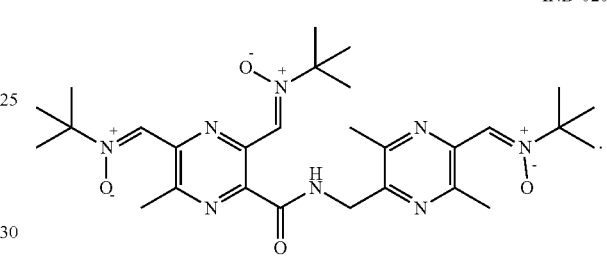

4. A pyrazine derivative or a pharmaceutically acceptable salt thereof, the pyrazine derivative having a formula V:

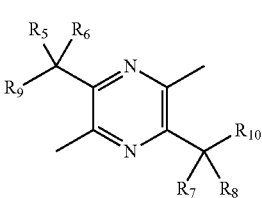

V wherein:

$R_5$, $R_6$, $R_7$, $R_8$, being the same or different, are each independently hydrogen, saturated or unsaturated alkyl, cycloalkyl, substituted or unsubstituted aryl, or heteroaryl;

$R_9$ and $R_{10}$, being the same or different, are each independently selected from the group consisting of R'''CONH, wherein R''' is a saturated or unsaturated alkyl, cycloalkyl, substituted or unsubstituted aryl, or heteroaryl group;

wherein, the alkyl is a C1-C10 alkyl, the cycloalkyl is a five-membered or six-membered cycloalkyl, the aryl is a single-ring aryl, the heteroaryl is a single-ring heteroaryl; the substitution group is $NH_2$, $NO_2$, $N(CH_3)_2$, $ONO_2$, F, Cl, Br, I, OH, $OCH_3$, $CO_2H$, $CO_2CH_3$, CN, aryl, or nitronyl.

5. The pyrazine derivative or a pharmaceutically acceptable salt thereof according to claim 4, the pyrazine derivative having a formula VI, VII or VIII:

VI

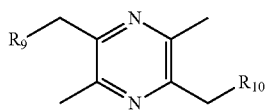

VII

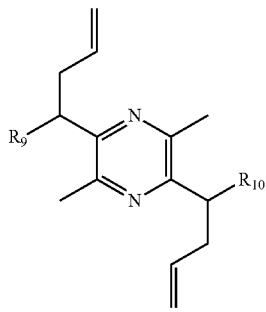

VIII

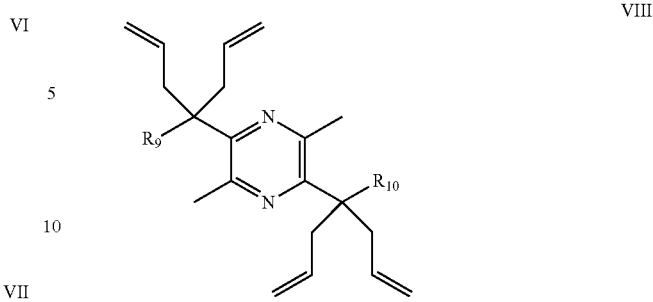

wherein:
in formula VI, $R_9$ and $R_{10}$, being the same or different, are each independently selected from the group consisting of R'''CONH, wherein R''' is saturated or un saturated alkyl, substituted or unsubstituted aryl, or heteroaryl;
in formula VII or VIII, $R_9$ and $R_{10}$, being the same or different, are each independently selected from the group consisting of hydrogen, R'''COO, and R'''CONH, wherein R''' is saturated or unsaturated alkyl, substituted or unsubstituted aryl, or heteroaryl, with a proviso that $R_9$ and $R_{10}$ cannot both be hydrogen.

6. The pyrazine derivative or a pharmaceutically acceptable salt thereof according to claim 5, wherein the pyrazine derivative has one of structures below:

IND-021

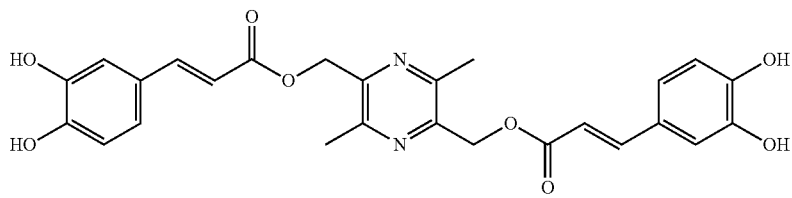

IND-022

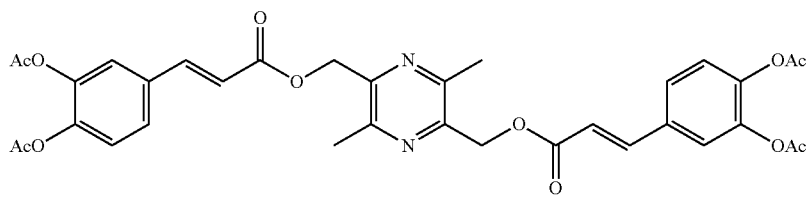

IND-023

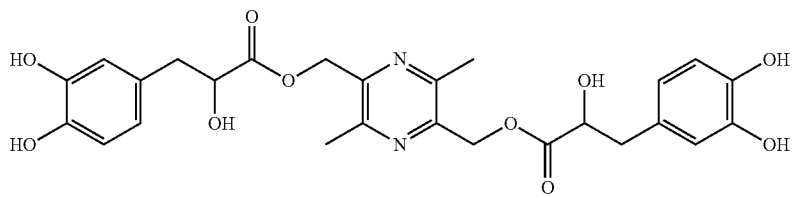

IND-024

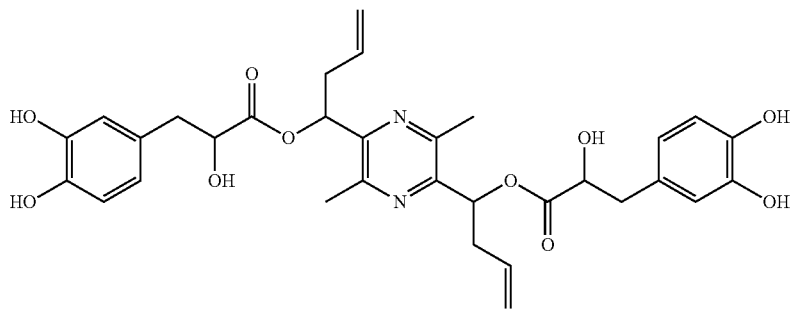

IND-025

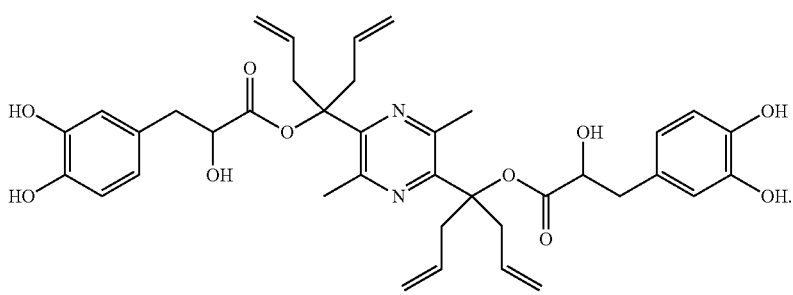

7. A method of preparation of the pyrazine derivative of claim 1, the method comprising:
tetramethylpyrazine is first reacted with NBS to give a ligustrazine mono-bromide; or
tetramethylpyrazine is oxidized by activated manganese dioxide to give a para-substituted tetramethylpyrazine dialdehyde derivative, which is subjected to selective reduction, bromination and aldehyde group protection to give a para-substituted tetramethylpyrazine derivative; and
the ligustrazine mono-bromide or para-substituted tetramethylpyrazine derivative is further reacted to give a respective product of the pyrazine derivative.

8. The method according to claim 7, comprising:
a) the ligustrazine mono-bromide or para-substituted tetramethylpyrazine derivative is reacted with triethyl phosphate to give a respective intermediate;
b) the tetramethylpyrazine dialdehyde derivative is reacted with ethylene glycol, with one of aldehyde groups being selectively protected, to give a product, which is further reacted respectively with the intermediate of step a) to give a respective tetramethylpyrazine coupling compound, which is deprotected under acidic conditions and then reacted with t-butylhydroxylamine to give a product of the pyrazine derivative.

9. The method according to claim 7, comprising:
the tetramethylpyrazine dialdehyde derivative is reacted with one or two of aldehyde groups being selectively reduced to give a monohydroxy derivative or a dihydroxy derivative;
the monohydroxy derivative or the dihydroxy derivative is each reacted with phosphorus tribromide to give a mono-bromo or dibromo derivative, respectively;
the mono-bromo derivative is condensed with a different carboxylic acid and then reacted with t-butylhydroxylamine, or the dibromo derivative is reacted with a different carboxylic acid or sodium carboxylate to give a product of the pyrazine derivative.

10. A method of treatment of diseases, comprising administration of a therapeutically effective amount of the pyrazine derivative or a pharmaceutical composition thereof according to claim 1, wherein the diseases are cardiovascular and cerebrovascular diseases, glutamate receptor related diseases, oxidative stress injury/free radical related diseases, neurodegenerative diseases or inflammatory infectious diseases;
wherein the cardiovascular and cerebrovascular diseases are cerebral apoplexy, hypoxic-ischemic brain injury, ischemic heart disease, angina pectoris, apoplexy sequelae, acute myocardial infarction, or myocarditis;

wherein the glutamate receptor related diseases are Alzheimer's disease, Parkinson's disease, Huntington's disease, amyotrophic lateral sclerosis, glaucoma, or dementia;
wherein the oxidative stress injury/free radical related diseases are stroke, epilepsy, Parkinson's disease, Huntington's disease, amyotrophic lateral sclerosis, Alzheimer's disease, hypoxic-ischemic brain damage, cerebral hemorrhage, dementia, ischemic heart disease, diabetes, or alcohol-induced liver disease;
wherein the neurodegenerative diseases are Alzheimer's disease, Parkinson's disease, amyotrophic lateral sclerosis, Huntington's disease, cerebellar atrophy, multiple sclerosis, primary lateral sclerosis or spinal muscular atrophy;
wherein the inflammatory infectious diseases are inflammatory bowel disease, cirrhosis, encephalomyelitis, meningitis, glomerulonephritis, myocarditis, uveitis, chalazion, keratitis, or optic neuritis ophthalmic diseases.

11. The A pyrazine derivative or a pharmaceutically acceptable salt thereof, the pyrazine derivative having a formula III:

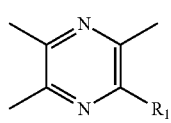

III wherein the pyrazine derivative has one of structures below:

IND-001

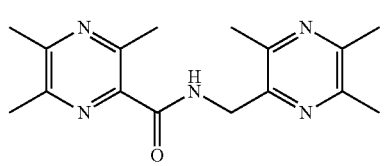

IND-006

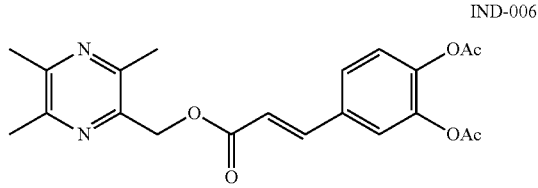

IND-018
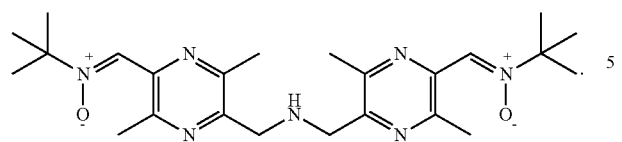
* * * * *